United States Patent
Dutta

(10) Patent No.: US 6,982,332 B2
(45) Date of Patent: Jan. 3, 2006

(54) HYBRID 2-AMINOTETRALIN AND ARYL-SUBSTITUTED PIPERAZINE COMPOUNDS AND THEIR USE IN ALTERING CNS ACTIVITY

(75) Inventor: Aloke K. Dutta, Novi, MI (US)

(73) Assignee: Wayne State University, Detroit, MI (US)

( * ) Notice: Subject to any disclaimer, the term of this patent is extended or adjusted under 35 U.S.C. 154(b) by 119 days.

(21) Appl. No.: 10/344,285

(22) PCT Filed: Jun. 7, 2002

(86) PCT No.: PCT/US02/18267

§ 371 (c)(1),
(2), (4) Date: Feb. 6, 2003

(87) PCT Pub. No.: WO02/098367

PCT Pub. Date: Dec. 12, 2002

(65) Prior Publication Data

US 2003/0195219 A1 Oct. 16, 2003

Related U.S. Application Data

(60) Provisional application No. 60/296,622, filed on Jun. 7, 2001.

(51) Int. Cl.
C07D 417/12 (2006.01)
C07D 403/12 (2006.01)
C07D 401/12 (2006.01)
C07D 295/13 (2006.01)

(52) U.S. Cl. .................. 544/253; 544/359; 544/363; 544/368; 544/392

(58) Field of Classification Search ................ 544/253, 544/359, 363, 368, 392; 514/252.13, 252.17, 514/253.06, 254.02, 255.03

See application file for complete search history.

(56) References Cited

U.S. PATENT DOCUMENTS 2,794,804 A 6/1957 Kushner et al.
6,087,346 A 7/2000 Glennon et al.
6,380,224 B1 * 4/2002 Dax et al. .................. 514/357

FOREIGN PATENT DOCUMENTS

WO WO 02/098367 A2 12/2002

OTHER PUBLICATIONS

Levant, Beth, Pharmacological Reviews, vol. 49, Issue 3, 231–252, Sep. 1997.*
Pinter MM, Rutgers AW, Hebenstreit E., J. Neural Transm. 2000; 107(11):1307–23, Medline abstract PMID: 11145006.*
Canon, J.G., Lee, T., Goldman, H.D., Costall, B., Naylor, R.J., "Cerebral Dopmine Agonist Properties of Some 2–aminotetralin Derivatives after Peripheral and Intracerebral Administration," J. Med. Chem., 20, 1111–1116, 1977.
McDermed, J., McKenzie, G., Phillips, A., "Synthesis and Pharmacology of Some 2–aminotetralins Dopamine Receptor Agonists," J. Med. Chem. 18, 362–367, 1975.
Levesque, D., Diaz, J., Pilon, C., Martres, M.-P., Giros, B., Souil, E., Schott, D., Morgat, J.-L., Schwartz, J.-C., Sokoloff, P., "Identification, Characterization, and Localization of the Dopamine $D_3$ Receptor in Rat Brain Using 7-[$^3$H]hydroxy-N,N-di-n-propyl-2–aminotetralin," Proc. Natl. Acad. Sci, U.S.A., 89, 8155–8159, 1992.
Alexander van Vliet, L., Tepper, P.G., Dijkstra, D., Damsma, G., Wikstrom, H. Pugsly, T.A., Akunne, H.C., Heffner, T.G., Glase, S.A., Wise, L.D., "Affinity for Dopamine $D_2$, $D_3$ and $D_4$ Receptors of 2–aminotetralins, Relevance of $D_2$ Agonist Binding for Determination of Receptor Subtype Selectivity," J. Med. Chem. 39, 4233–4237, 1996.
John Murray, P., et al., "A Novel Series of Arylpiperazines with High Affinity and Selectivity for the Dopamine $D_3$ Receptor," Bioorg. Med. Chem. Lett., 5, 219–222, 1995.

(Continued)

*Primary Examiner*—Thomas C. McKenzie
(74) *Attorney, Agent, or Firm*—Brooks Kushman P.C.

(57) ABSTRACT

Compounds exhibiting CNS activity in mammalian species, having the structure

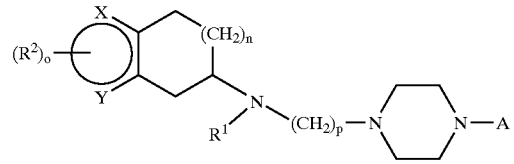

wherein A is an optionally heterocyclic 5 or 6 membered aromatic ring system;

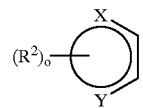

$R^2$ is an organyl group substituent or two $R^2$ together may form a fused ring system,
o is an integer from 0 to 4, the upper limit of o bounded by the num er of available substitutent sites on said optionally heterocyclic 5 or 6 membered aromatic ring structure;
n is an integer from 0 to 2;
$R^1$ is an organyl group;
p is 1 to 4;
wherein one $(CH_2)_n$ group may be replaced by O or S;
or a pharmaceutically acceptable derivative thereof;
The compounds exhibit activity in dopamine transporter systems, and in p rticular a high differential activity between the D3 and D2 receptors.

8 Claims, No Drawings

OTHER PUBLICATIONS

Teran, C., et al., "Phenylpiperazine Derivatives with Strong Affinity for 5HT1a, D2A and D3 Receptors," Bioorg. Med. Chem. Lett., 8, 3567–3570, 1998.

*Boyfield, I., et al., "A Novel Series of 2–aminotetralins with High Affinity and Selectivity for the Dopamine $D_3$ Receptor," Bioorg. Med. Chem. Lett., 7, 1995–1998, 1997.

Yuan, J., et al., "NGB 2904 and NGB 2849: Two Highly Selective Dopamine $D_3$ Receptor Antagonist," Bioorg. Med. Chem. Lett., 8, 2715–2718, 1998.

Homan, E.J., et al., "2–aminotetralin–derived Substituted Benzamide with Mixed Dopamine $D_2$, $D_3$, and Serotonin 5–HT1A Receptor Binding Properties: A Novel Class of Potential Atypical Antipsychotic Agents," Bioorg. Med. Chem.

Avenell, K.Y., et al., Heterocyclic Analogues of 2–aminotetralins with High Affinity and Selectivity for Dopamine $D_3$ Receptor, Bioorg. Med. Chem. Lett., 9, 2715–2720, 1999.

Pugsley, T.A., et al., Pharmacol. Exp. Ther., 275, 1355–1366, 1995.

*Pilon, C., et al., Eur. J. Pharmacol., 268: 129–139, 1994.

Millan, M.J., et al., J. Pharmacol. Exp. Ther., 286, 1341–1355, 1998.

Ravina, E., et al., J. Med. Chem., 43, 4678–4693, 2000.

*Watts, V.J., et al., Eur. J. Pharmacol., 239, 271–273, 1993.

*Dutta, A.K., et al., Bioorg. Med. Chem. Lett., 12:4:619–6, 2002.

Kula, N.S., et al., Cell. Mol., Neurobiol., 14, 185–191, 1994.

* cited by examiner

HYBRID 2-AMINOTETRALIN AND ARYL-SUBSTITUTED PIPERAZINE COMPOUNDS AND THEIR USE IN ALTERING CNS ACTIVITY

The present application is a 371 of PCT application PCT/US02/18267 filed Jun. 7, 2002 and further claims the benefit of U.S. Provisional Application Ser. No. 60/296,622, filed Jun 7, 2001.

BACKGROUND OF THE INVENTION

1. Field of the Invention

The present invention is directed to central nervous system pharmaceutically active compounds having both aryl-substituted piperazine and aminotetralin moieties, 5 or 7 membered cycloaliphatic ring homologues thereof, or open chain analogues thereof; and to their pharmacological use. These hybrid compounds exhibit high activity at various dopamine and serotonin receptor subtypes. Certain of the compounds exhibit high differential selectivity between D2 and D3 receptor subtypes.

2. Background Art

The dopamine receptors of the brain have proven fertile targets for pharmacological treatment of numerous central nervous system ("CNS") disorders, including psychotic disorders such as schizophrenia and neurodegenerative disorders such as Parkinson's disease.[8]

In the last decade and a half, advances have been made in development of drugs specific for dopamine receptor subtypes, and in the development of novel pharmaceutically active compounds for their characterization.[1-3] In addition, in 1990, a new dopamine subtype receptor now known as the D3 receptor was discovered and subsequently cloned from rat complimentary DNA libraries using probes derived from the D2 receptor subtype.[4,5] This new D3 receptor subtype belongs to the short form of D2 receptor subtype, and bears close resemblance to the latter.[5,6,7]

Therapies involving D2-specific drugs often are associated with side effects like EPS, Tardive dyskinesia, believed to originate from blockage of D2 receptors in the striatal region of the brain.[9] Studies probing the location of D3 receptors have shown that the distribution of the latter is different from the distribution of D2 receptors. In situ hybridization studies showed a lack of adequate presence in the caudate putamen area of the striatal section, and a dominant presence in the nucleus accuinbens area.[10] These different distribution patterns render the D3 receptors unique targets for drug development. D3-specific antagonists and agonists are expected to have numerous applications in treatment of psychotic disorders and neurodegenerative diseases without the undesirable side effects associated with pharmacology of the D2 receptor.[11,12,13] Recent studies have shown that D3 specific compounds may also have therapeutic use in treatment of cocaine[8] addiction.[14,15,16] Efforts have thus been made to develop D3 specific drug candidates.

For example, 2-aminotetralins have been regarded as potent and selective agonists for D2 receptors.[17-20] However, 7-OH-DPAT and PD 128907, both aminotetralins, have shown preferential activity at the D3 receptor.[21] Several other aminotetralin-related derivatives were also found to have such preferential selectivity.[22] Aryl piperazines have also been demonstrated to have activity toward the D2 and D3 receptors,[23,24] and some of these were found to have both high affinity and selectivity for the D3 receptor.[26] One such compound is GR103691,[25] containing a N-(methoxyphenyl)piperidine moiety linked to a 4'-acetyldiphenyl moiety through an N-alkyl-N-urethane linking group. A series of 8-hydroxy-2-aminotetralins bearing benzamide moieties have also been shown to have selective affinity for the D3 receptor,[27,28] and a thiaza heterocyclic analog was shown to have high affinity and selectivity for this receptor subtype.[28]

It would be desirable to provide additional pharmaceutically active compounds which exhibit high levels of CNS activity, for example, with respect to the dopaminergic receptors as well as the serotoninergic receptors. It would be further desirable to provide drug candidates which exhibit high activity with respect to the D3 receptor subtype, and in particular to provide drug candidates which exhibit high selectivity between the D2 and D3 subtypes.

SUMMARY OF THE INVENTION

It has now been surprisingly discovered that hybrid compounds containing both aminotetralin moieties, homologous 5 or 7 membered cycloaliphatic ring moieties, or their heterocyclic and/or open chain analogues, in conjunction with an aryl-substituted piperazinyl moiety, exhibit high CNS activity, in particular high D3 affinity and/or D3/D2 selectivity.

DETAILED DESCRIPTION OF THE PREFERRED EMBODIMENTS

The subject invention compounds are hybrid compounds containing both an aminotetralin moiety or related structure as hereafter defined, and an N'-aryl piperazinyl structure, linked to the "aminotetralin" structure by an alkylene bridge. The subject compounds have the following structure

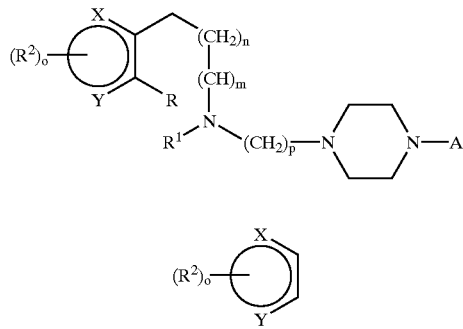

where is an aromatic and optionally heterocyclic ring system containing 5 or 6 ring atoms and up to two heteroatoms selected from the group consisting of N, O, and S, this aromatic ring system optionally substituted by o $R^2$ groups, where o is 0, 1, 2, 3, or 4, the upper limit bounded by the number of available substituent sites. The $R^2$ groups are organyl groups preferably selected from among $C_{1-8}$ alkyl, $C_{2-8}$ alkenyl, $C_{1-8}$ alkynyl, $C_{4-8}$ cycloalkyl, $C_{4-8}$ cycloalkenyl; $C_{6-10}$ aryl, —$NR^4_q$ where $R^4$ individually are H or organyl groups, preferably H, $C_{1-8}$ alkyl, $C_{2-8}$ alkenyl, $C_{4-8}$ cycloalkyl, $C_{4-8}$ cycloalkenyl, $C_{6-10}$ aryl and q is 2 or 3, with the proviso that when q is 3, the group bears a positive formal charge; —NH—C(O)—$R^4$, —NH—C(O)—$NR^4_2$, and related compounds wherein the hydrocarbon groups in each case may optionally by substituted with —CN, $C_{1-4}$ lower alkyl, —$OR^4$, halo, particularly fluoro and/or chloro, —$CF_3$, and the like.

$R^4$ may also be arylsulfonyl, preferably 4-chlorophenylsulfonyl, 3,4-dichlorophenylsulfonyl; 4-(trifluoromethyl)phenylsulfonyl; $R^6$—Ar—$SO_2$ where $R^6$ is an electron withdrawing or electron donating substituent and Ar is an aromatic or heteroaromatic moiety; or keto, preferably phenylketo, 4-(trifluoromethyl)phenylketo, or aceto. Two $R^2$ may form part of a fused cycloalkyl or aryl ring, optionally containing N, O, or S heterocycles. For example, two $R^2$ may combine to form the structures

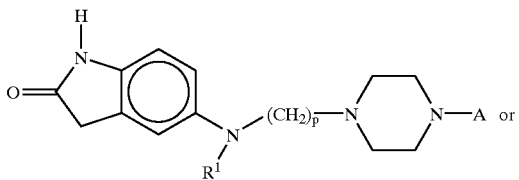

or

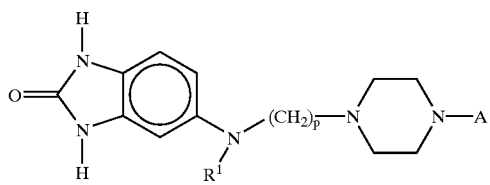

R is H, $C_{1-4}$ lower alkyl, $C_{1-4}$ lower alkoxy, —CN, or is a methylene bonded to $(CH)_m$, forming a 5 to 7 membered ring structure. In open chain analogues, m is 0 and R is not a methylene group bonded to $(CH)_m$.

The compound contains $n(CH)_2$ groups, n being such that when m=0, n will be 0, 1 or 2 and R will be a methylene group linking the aromatic 5 to 7 membered ring with the CH group to form a cycloaliphatic ring structure which will contain 5 to 7 carbon atoms, or n is such that when the compound is an open chain analog, n may range from 0 to 4. Thus, when m=1 and n=1, the leftmost moiety in the formula will be an aminotetralin or heteroaryl analogue thereof.

$R^1$ is an organo group, preferably selected from among $C_{1-8}$ alkyl, $C_{2-8}$ alkenyl, $C_{2-8}$ alkynyl, $C_{4-8}$ cycloalkyl, $C_{4-8}$ cycloalkenyl, $C_{6-10}$ aryl, each of the foregoing alkyl, alkenyl, alkynyl, cycloalkyl, etc. groups optionally halo substituted, preferably fluoro and/or chloro substituted, or substituted by —CN, $C_{1-4}$ lower alkoxy, $C_{1-4}$ acyloxy, $C_{1-4}$ acyl, —C(O)—$R^4$, or —$R^5$—NH—$SO_2$—$NR^4_r$, where $R^5$ is $C_{1-8}$ alkylene and r is 2 or 3, with the proviso that when r is 3, the nitrogen of the $NR^4_r$ group will bear a positive formal charge; —$R^5$—NH—C(O)—$R^4_r$; —$R^5$—$NR^4_r$; —$R^5$—Ar where Ar is an aryl ring system, preferably a $C_{6-10}$ aryl ring system, optionally including one or more heteroatoms, preferably phenyl, thienyl, pyridyl, biphenyl, or naphthyl.

The nitrogen of the aminotetralin or its heterocyclic and/or open chain analog is bonded to a nitrogen of the piperazinyl group through the intermediacy of $p(CH_2)$ groups, where p is 1 to 4, preferably 2 to 4.

A is an aryl group optionally containing one or more heteroatoms bonded to the remaining nitrogen of the piperazinyl group. The aryl group may consist of from 1 to 4 rings, optionally fused, and optionally substituted by $C_{1-4}$ alkyl, $C_{2-4}$ alkenyl, $C_{5-7}$ cycloalkyl, $C_{5-7}$ cycloalkenyl, halo, preferably fluoro or chloro, $C_{1-4}$ aldehyde, —$NR^4_q$ and like groups. It should be noted that unsaturated groups such as alkenyl and cycloalkenyl include multiply unsaturated groups such as alkadienyl and cycloalkadienyl. Alkyl and cycloalkyl groups herein also include aryl-substituted alkyl and cycloalkyl groups, while aryl groups also include alkyl and cycloalkyl-substituted aryl groups. A is preferably optionally substituted thienyl, pyridinyl, phenyl, biphenyl, or naphthyl, more preferably phenyl and biphenyl. All the substituent classes of R, $R^1$, $R^2$, and $R^4$ may be used as substituents on optionally substituted A. Preferred substituents include $C_{1-4}$ alkyl, —CN, halo, $C_{1-4}$ lower alkoxyl, and $NH_2SO_2R^4$, $CF_3$, arylsulfonyl, arylsulfonamide, etc., more preferably o-$OCH_3$, 2,3-dichloro, and p-$NHSO_2CH_3$.

Preferred hybrid compounds include those having the structure I and II below:

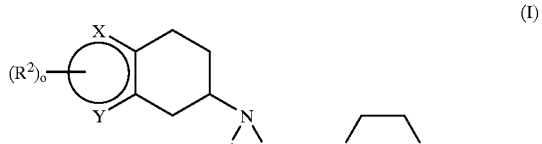

(I)

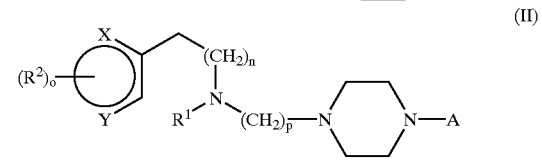

(II)

where I represents an aminotetralin or heterocyclic analog thereof, while II represents an open chain, optionally heterocyclic analog thereof, i.e. a compound similar in overall structure to I but where the saturated aminotetralin ring is an open chain rather than cyclic moiety. In these and the foregoing formulae, X and Y are moieties which complete a 5 or 6 membered aromatic ring system. For example, X together with Y may be $(CH)_4$, forming a phenyl ring, or may be N—CH—S forming an thiazole ring. It is preferably that the X,Y-containing ring be a phenyl, aminothiazolyl, or aminopyridyl ring system. Preferred "closed ring" aminotetralin moiety compounds thus include II, III, and IV below:

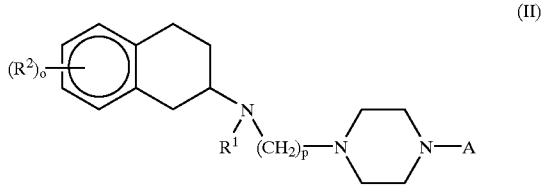

(II)

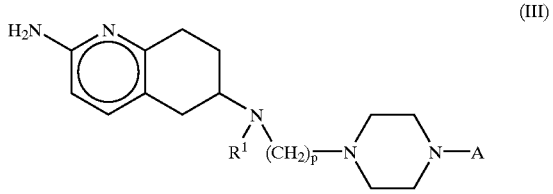

(III)

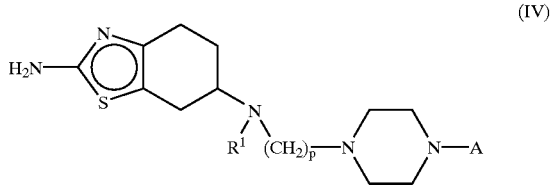

(IV)

In addition, the saturated aminotetralin ring or its 5 to 7 membered homologue in such ring systems may also include O or S heteroatoms, i.e. structure V below:

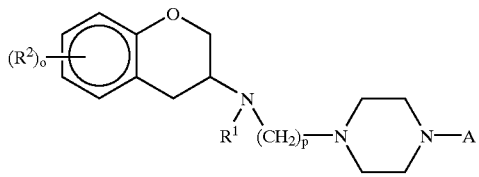

Preferred open chain analogues have the structure VI:

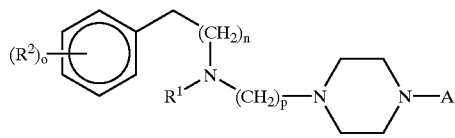

Additional preferred open chain structures include

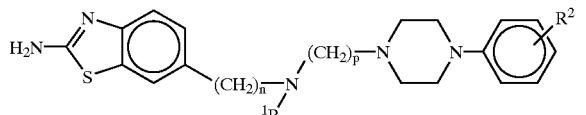

and

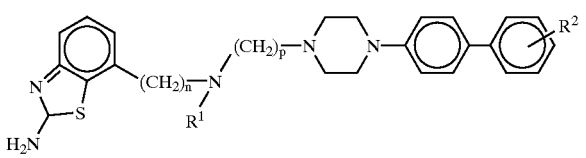

Typical dosages for mammalian species may vary from 0.001 mg/Kg of body weight to about 100 mg/Kg of body weight, preferably 0.01 mg/Kg to 5 mg/Kg. The actual amount will vary depending upon the particular CNS activity desired to be altered, and the desired degree of alteration. The upper limits may, as with virtually all drugs, be limited by toxicity of the drug or its metabolites, or by the presence of unwanted side effects. The drugs may be administered in any form, but preferably in the form of tablets or capsules with appropriate excipients. Dosages, forms of administration, etc., can be readily determined by those skilled in the art.

All the compounds described above can be synthesized by techniques well known to those skilled in organic synthesis. Among the compounds synthesized are those included in Tables 1, 2, and 3 below. Table 1 includes aminotetralin hybrids per se, while Table 2 includes heterocyclic analogs thereof. In both Table 1 and Table 3, the leftmost aromatic ring is a phenyl ring, i.e., as shown in structures II and VI, respectively. Table 3 includes "open chain" analogues. In the tables, the substituent headings are those the corresponding to structural formulae II (Table 1); I (Table 2); and VI (Table 3). In Table 2, the "Ring" column specifies the heterocyclic ring portion which includes X and Y of structure I. The compounds identified in the tables represent compounds tested for CNS activity, the results of which are presented in Tables 4–8. However, additional compounds have been synthesized as well, as reported herein.

The compounds may be used per se or as pharmaceutically acceptable derivatives. The latter term includes salts, esters, and other derivatives generally considered acceptable by pharmaceutical standards.

TABLE 1

| Compound | $R^2$ | $R^1$ | p | A |
|---|---|---|---|---|
| 8 | 7-OH | 3-cyanopropyl | 4 | phenyl |
| 10a | 7-OH | (4-benzoylamino)butyl | 4 | phenyl |
| 10b | 7-OH | (2-benzoylamino)ethyl | 4 | phenyl |
| 12a | 7-OH | propargyl | 2 | phenyl |
| 12b | 7-OH | propargyl | 4 | phenyl |
| 15a | 7-OH | propyl | 2 | phenyl |
| 15b | 7-OH | propyl | 4 | phenyl |
| 19a | 7-OH | propyl | 4 | 2,3-dichlorophenyl |
| 19b | 7-OH | propargyl | 4 | 2,3-dichlorophenyl |

TABLE 2

| Compound* | Ring | $R^2$ | $R^1$ | A |
|---|---|---|---|---|
| 23 | (pyrazine) | 2-$NH_2$ | propyl | phenyl |
| 25 | (thiazole) | 2-$NH_2$ | propyl | phenyl |

*p is 2 in each of the compounds of Table 2.

TABLE 3

| Compound | $R^2$ | $R^1$ | n* | p | A |
|---|---|---|---|---|---|
| 29a | 4-$NH_2$ | propyl | 1 | 2 | phenyl |
| 29b | 3-$NH_2$ | propyl | 1 | 2 | phenyl |
| 30a | 4-$NHSO_2$-ϕ-4Cl | propyl | 1 | 2 | phenyl |
| 30b | 3-$NHSO_2$-ϕ-4Cl | propyl | 1 | 2 | phenyl |

*m = 0 in all the open-chain compounds in Table 3.

CNS activity was assessed by in vitro testing on cloned human dopamine and serotonin receptors by standard techniques. These techniques are known by those skilled in the art to reflect in vivo activity. Techniques and their relationship to CNS activity are well known.[29-35]

Initial efforts resulted in the design and synthesis of novel compounds 12b and 15b. In designing of 10a–b it was decided to incorporate an additional benzamide moiety into the structural base to enhance the binding of these novel analogs by accessing the accessible domains in the receptor. It was conceived that such moieties might play a role in selectivity as well as activity.

These compounds were characterized for their binding at the cloned dopamine $D_1$, $D_2$, $D_3$ and $D_4$ receptor subtypes and also at the $5HT_{1A}$, $5HT_{2A}$ and $5HT_{2C}$ serotonin receptors subtypes (Tables 4 to 8). Compounds 15b and 12b with a 4-methylene long linker exhibited marked potency for the both D2 and D3 receptors and much weaker activity for the D1 receptor (Table 4). In addition, compounds 12b and 15b showed good affinity at the D4 receptor and were full agonists at this receptor. In the functional assay, compounds 15b and 12b showed preferential agonist activity at the D3 receptor while showing partial agonism at the D3 receptor (Table 7). On the other hand, compound 15a with a shorter, two-methylene chain linker, was more selective at the D3 receptor (Tables 1 and 5). The selectivity of 15a in this regard was more than two fold than the standard 7-OH-DPAT when assessed by the protocol used in Table 4 and was one of the most selective compounds in this series. The replacement of the phenyl group in 15b by a 2,3-dichlorophenyl moiety resulted in 19a which showed improved selectivity for the D3 receptor (15 vs. 1) compared to 15b. Replacement of the phenol moiety in compound 15a by a thiazolidinium moiety in 25 also resulted in much greater selectivity for the D3 receptor (Table 4; Table 8).

Amide-substituted piperazine derivatives 10a–b, were less active either at the dopamine or at the serotonin receptor subtypes while the cyano compound 8 showed modest activity at these receptors (Table 1 and 3).

Various compounds were tested against serotonin receptor subtypes. As shown in Table 6 these compounds were weak in their binding to the serotonin receptor subtypes except compounds 15a–b and 12a–b which showed good potency at the $5HT_{1A}$ receptor.

Open chain analog compounds 30a–b were also synthesized and biologically characterized. SAR results indicate that compounds 30a–b with an electron withdrawing substituent are more potent than compounds not containing such a substituent (Table 5).

Biological Methods:

Biological studies were carried out with cloned human dopamine and serotonin receptors as described below.

D1 Receptor

LHD1 cells (human receptor) are grown and prepared as described for the HA7 cells as described hereafter. The final pellet is resuspended at 5 mg protein/80 ml in 50 mM Tris-HCl containing 120 mM of NaCl, 5 mM of KCl, 2 mM of $CaCl_2$, and 1 mM of $MgCl_2$, pH 7.4. To wells containing 100 µl of test drug or buffer and 100 ml of [$^3$H]SCH 23390 (0.18 nM final conc.), is added 0.8 ml of cell homogenate (0.05 mg protein/well), and the plates are incubated at 250° C. for 60 min. Nonspecific binding is determined with 1 µM of SCH 23390.

D2 and D3 Receptors

CHOp-cells (human receptors) are grown to confluence in α minimum essential medium (α MEM) containing 10% fetal calf serum, 0.05% pen-strep, and 600 µg/ml of G418. The cells are scraped from the 100 by 20 mm plates and centrifuged at 500. g for 5 min. The pellet is homogenized by polytron in 50 mM Tris-HCl, pH 7.7, and centrifuged at 27,000·G for 12 min. The pellet is resuspended in 50 mM Tris, $D_2$ at 5 mg protein/ml, $D_3$ at 1 mg protein/ml, and stored at −70° C. in 1-ml aliquots.

On the day of the experiment, CHOp-$D_2$ or CHOp-$D_3$ cells are thawed, resuspended in 50 mM Tris, and centrifuged at 27,000·G for 12 min. The pellet is then resuspended at 5 mg protein/80 ml ($D_2$) and 1 mg protein/80 ml ($D_3$) in 50 mM Tris containing 120 mM of NaCl, 5 mM of KCl, 1.5 mM of $CaCl_2$, 4 mM of $MgCl_2$, and 1 mM of EDTA, pH 7.4. Then 0.8 ml of cell homogenate (0.05 and 0.01 mg protein/well, $D_2$ and $D_3$ respectively) is added to wells containing 100 µl of the test drug or buffer and 100 µl of [$^3$H]YM-09151-2 (0.21 nM final conc.). Nonspecific binding is determined with 1 mM of chlorpromazine. The plates are incubated at 25° C. for 60 min before filtration and counted as usual. The filters are soaked in 0.1% PEI before filtering.

D4 Receptor

CHO D4.4 cells (human receptors) are grown to confluence in $D_4$ Puromycin medium containing 2 µg/ml puromycin, 5% fetal calf serum and 5% supplemented calf serum and 0.5% pen-strep. The cells are harvested as described for $D_2$ and $D_3$ cells and used at a concentration of 0.15 mg protein/well in the [$^3$H]YM-09151-2 binding assay.

5-HT1A Receptor

HA7 cells (human receptor) are grown to confluence in DMEM containing 10% fetal calf serum, 0.05% penicillin-streptomycin (pen-strep), and 400 mg/ml of G418. The cells are scraped from the 100 by 20 mm plates and centrifuged at 500·G for 5 min. The pellet is homogenized in 50 mM Tris-HCl, pH 7.7, with a polytron, centrifuged at 27,000·G and resuspended at 10 mg protein/ml in the same buffer. The homogenate is then stored at −70° C. in 1-ml aliquots.

The thawed cells are washed once and resuspended at 10 mg protein/80 ml in 25 mM Tris-HCl containing 100 µM of ascorbic acid and 10 mM of nialamide at pH 7.4. The assay is performed in triplicate in a 96-well plate. To 100 µl of [$^3$H]8-OH-DPAT (0.5 nM final conc), 100 ml of test compound or buffer and 0.8 ml of cell homogenate (0.1 mg protein/well) is added to each well by a Tomtec Quadra 96. Nonspecific binding is defined using 1 µM dihydroergotamine. The plates are incubated at 25° C. for 60 min, then filtered. The incubation is terminated by rapid filtration through glass fiber filter paper on a Tomtec cell harvester. The filters are washed four times with ice-cold 50 mM Tris-HCl, pH 7.7, dried overnight, bagged with 10 ml scintillation cocktail before counting for 2 min. on a Wallac Betaplate 1205 liquid scintillation counter.

Results of testing of several representative compounds for binding affinity at the D1, D2, D3 and D4 dopaminergic receptor subtypes are presented in Table 4, along with 7-OH DPAT, known to have high affinity for the D3 receptor subtype and relatively high differential affinity between the D3 and D2 receptor subtypes. In interpreting the table, it should be noted that low values represent high affinity, i.e. high displacement of the reference binding ligand. Higher D2/D3 ratios thus represent higher relative affinity for the D3 receptor subtype as compared with the D2 receptor subtype. Preferred compounds have at least 1.5 times the D2/D3 ratio of 7-OH DPAT when measured by the same protocol.

TABLE 4

Binding Affinity at the Cloned Human D1, D2, D3 and D4 Receptors

| Compound | Ki(nM), D1 [$^3$H]SCH23390 | Ki(nM), D2 [$^3$H]YM-09151-2 | Ki(nM), D3 [$^3$H]YM-09151-2 | Ki(nM), D4 | D2/D3 |
|---|---|---|---|---|---|
| 7-OH-DPAT | 2548 ± 1082 | 16 ± 2.0 | 1.5 ± 0.4 | | 10.6 |
| 8 | 3217.5 ± 7.77 | 89.79 ± 32.53 | 75.78 ± 6.29 | 142.26 ± 6.50 | 1.18 |
| 10a | 3734.5 ± 272 | 119.16 ± 1.45 | 313.19 ± 6.47 | 136.9 ± 10.19 | 0.38 |
| 10b | 2947.86 ± 237.81 | 110.94 ± 32.19 | 84.62 ± 1.55 | 35.63 ± 1.42 | 1.30 |
| 12a | 662.6 | 65.5 | 23.48 | | 2.8 |
| 12b | 676.77 ± 34 | 6.54 ± 1.14 | 6.58 ± 1.15 | 28.93 ± 4.41 | 1 |
| 15a | >10000 | 75.48 | 3.2 | | 25 |

TABLE 4-continued

Binding Affinity at the Cloned Human D1, D2, D3 and D4 Receptors

| Compound | Ki(nM), D1 [³H]SCH23390 | Ki(nM), D2 [³H]YM-09151-2 | Ki(nM), D3 [³H]YM-09151-2 | Ki(nM), D4 | D2/D3 |
|---|---|---|---|---|---|
| 15b | 6119.68 ± 932.83 | 3.37 ± 0.78 | 3.47 ± 0.08 | 25.66 ± 25.66 | 1 |
| 19a | 4062.6 | 31.53 | 2.66 | | 15 |
| 19b | 11718.28 | 28.09 | 12.69 | | 2.3 |

Table 4 indicates that all of the compounds tested had relatively high affinity for the D2, D3, and D4 receptor subtypes. Most had little affinity for the D1 receptor. Thus, all these compounds would be expected to exhibit CNS activity in vivo. Particularly noteworthy are compounds 15a and 19a, which exhibit considerably lower D1 receptor activity relative to 7-OH DPAT, and even higher activity differential as between the D2 and D3 receptors.

Various open chain analogues, those identified in Table 3, were also tested with respect to their binding affinities at the D2 and D3 receptors, as compared to 7-OH DPAT. The results are presented in Table 5.

TABLE 5

Binding Affinity at the Cloned Human D2 and D3 Receptors

| Compound | Ki(nM), D2 [³H]Spiperone | Ki(nM), D3 [³H]Spiperone |
|---|---|---|
| (+)-7-OH-DPAT | 538 ± 108 | 5.00 ± 1.18 |
| 29a | 25,553 ± 2,898 | 1,152 ± 130 |
| 29b | 23,517 ± 2,097 | 1,478 ± 247 |
| 30a | 702 ± 22 | 5.98 ± 0.70 |
| 30b | 552 ± 31 | 36.8 ± 5.4 |

TABLE 6

Binding Affinity at the Cloned Human 5HT1A, 5HT2A and 5HT2C Receptors

| Compound | Ki (nM), 5HT1A [³H]8-OH-DPAT | Ki (nM), 5HT2A [³H]Ketanserin | Ki (nM), 5HT2C [³H]Mesulergine |
|---|---|---|---|
| 7-OH-DPAT | 193 ± 3.4 | >10,000 | >10,000 |
| 8 | 88.31 ± 0.40 | 700.77 ± 16.78 | >10,000 |
| 10a | 171.48 ± 32.17 | 1231.23 ± 217 | >10,000 |
| 10b | 163.98 ± 27.48 | 287.44 ± 50.24 | >10,000 |
| 12a | 27.64 | 160.6 | 2693.4 |
| 12b | 15.25 ± 3.34 | 260.23 ± 41.94 | 3222.88 ± 52.90 |
| 15a | 21.42 | 1541.59 | >10,000 |
| 15b | 18.47 ± 2.46 | 1784.26 ± 614.31 | >10,000 |
| 19a | 40.56 | 355.79 | 638.54 |
| 19b | 64.38 | 160.22 | 264.28 |

Potential as dopaminergic agonists was assayed by ³H-thymidine incorporation by standard techniques. The results are presented in Table 7.

TABLE 7

Evaluation of Agonist Potency by [³H]Thymidine Incorporation Experiment

| Compound | D2 EC50 (nM) | % Maxm Stim | D3 EC50 (nM) | % Maxm Stim | D4 EC50 (nM) | % Maxm Stim |
|---|---|---|---|---|---|---|
| 7-OH-DPAT | 4.2 ± 2.2 | | 0.9 ± 0.6 | | | |
| 8 | 74.49 ± 32.91 | 54.09 ± 4.82 | 68.11 ± 36.70 | 67.07 ± 1.93 | 54.76 ± 18.60 | |
| 10a | 115.28 ± 20.22 | 44.91 ± 0.84 | 110.23 ± 33.27 | 44.06 ± 11.55 | 32.21 ± 2.51 | 51.08 ± 1.72 |
| 10b | 97.16 ± 47.74 | 27.03 ± 5.54 | 104.33 ± 57.28 | 50.93 ± 12.63 | 26.74 ± 10.55 | 71.36 ± 10.17 |
| 12a | 6.18 ± 0.18 | 87.20 ± 2.16 | 1.25 ± 0.08 | 94.53 ± 6.17 | | |
| 12b | 3.55 ± 1.34 | 85.01 ± 6.26 | 0.25 ± 0.03 | 71.69 ± 10.56 | 23.92 ± 3.57 | 85.15 ± 17.64 |
| 15a | 1.59 ± 0.06 | 104.66 ± 11.33 | 0.97 ± 0.02 | 84.62 ± 10.75 | | |
| 15b | 3.21 ± 0.46 | 120.72 ± 26.15 | 0.91 ± 0.46 | 74.92 ± 9.05 | 22.53 ± 10.98 | 102.81 ± 20.21 |
| 19a | 8.31 ± 0.69 | 80.09 ± 8.15 | 6.49 ± 2.46 | 85.67 ± 1.19 | | |
| 19b | 11.81 ± 1.84 | 85.66 ± 9.15 | 3.08 ± 1.09 | 90.34 ± 15.50 | | |

Noteworthy is the exceptionally low affinity of compounds 29a and 29b for the D2 receptor, while showing some activity at the D3 receptor, and compound 30a, which exhibits differential binding affinity between the D2 and D3 receptors which is higher than that of 7-OH DPAT.

The compounds tested against dopaminergic receptors and reported in Table 4 were also tested for binding affinity to the cloned human 5HT1A, 5HT2A, and 5HT2C serotonin receptors. A wide range of binding activity and differential binding activities considerably different from the activity exhibited by 7-OH DPAT is evident from the results presented in Table 6.

The mitogenesis study results presented in Table 7 assay the ability of these ligands to act as agonists or antagonists. The EC50 values thus indicate intrinsic activities or functional activities of these compounds. The value of % maximum stimulation indicates whether a compound is a partial agonist or full agonist. Generally, a value greater than 80% is considered as a full agonist and anything less than 80% is considered as a partial agonist. A compound will be considered antagonist if it produces a negative result (no [3H] thymidine incorporation) in the assay. All the compounds reported in Table 7 are either full agonists or partial agonists.

Inhibition constants for binding to cloned D2L and D3 receptors expressed in HEK cells by displacing [³H] spip erone were measured for several compounds. The results are presented in Table 8 below.

TABLE 8

Inhibition Constants for Binding to the Closed D2L and D3 Receptors Expressed in HEK Cells by Displacing [$^3$H]spiperone

| Compound | D2L HEK Cells [$^3$H]spiperone Ki (nM) | D3 HEK Cells [$^3$H]spiperone Ki (nM) | D2L/D3 |
| --- | --- | --- | --- |
| (+)-7-OH-DPAT | 538 ± 108 | 5.00 ± 1.18 | 107.6 |
| 8 | 622 ± 102 | 50.2 ± 7.1 | 12.4 |
| 10a | 782 ± 42 | 756 ± 48 | 1 |
| 10b | 354 ± 2 | 55.7 ± 5.5 | 6.3 |
| 12a | 245 ± 26 | 14.2 ± 1.7 | 17.2 |
| 12b | 68.4 ± 7.6 | 1.40 ± 0.14 | 48.9 |
| 15a | 213 ± 26 | 1.75 ± 0.34 | 121.7 |
| 15b | 114 ± 8 | 3.79 ± 0.40 | 30 |
| 19a | 8.78 ± 0.81 | 2.26 ± 0.50 | 3.8 |
| 19b | 7.37 ± 0.27 | 3.59 ± 0.58 | 2.0 |
| 19c | 27.4 ± 1.0 | 1.13 ± 0.04 | 24.2 |
| 23 | 1120 ± 144 | 22.3 ± 2.3 | 50 |
| 25 | 2080 ± 162 | 4.14 ± 0.55 | 502 |

Synthetic Procedures

A general synthetic scheme may be described as follows. Phenylpiperazine on N-alkylation with N-(4-bromoalkyl) phthalimide in presence of a base furnished 3a–b which on reaction with hydrazine released amine 4a–b. Reductive animation reaction of amine 4a–b with 7-methoxytetralone under standard conditions furnished amine 5a–b in good yield. N-Alkylation with bromocyanide resulted in cyano compounds 6a–b which were converted into amines 7a–b by reaction with lithium aluminum hydride (LAH). Demethylation of 6a with $BBr_3$ produced compound 8. Conversion of amines 7a–b to benzamide derivatives followed by demethylation produced compounds 10a–b. Similarly alkylation of 5a–b with propyl bromide produced N-alkylated derivatives which on demethylation produced final target compounds 12a–b. N-Acetylation of 5a–b followed by reduction with LAH furnished 14a–b. Demethylation of 14a–b produced final 15a–b. The dichloro compounds were synthesized in a similar manner.

Amine 4a was reacted with two isomeric nitrophenylacetic acid derivatives respectively to produce 26a–b which were converted to 28a–b by first reduction with $BH_3$ generated in situ by reaction of $BF_3$ with $NaBH_4$, followed by reaction with propionyl chloride to produce the intermediate amides. Final amine targets 29a–b were produced by reduction of the nitro group in compounds by catalytic hydrogenation followed by borane reduction The compounds 29a–b were converted into targets 30a–b by reacting with 4-chlorophenylsulfonyl chloride. Amine 4a was reacted with 4-fluoropheneacetyl chloride to produce amide 26 which on reduction with lithium aluminum hydride followed by N-propylation produced the target 27. These reaction are presented in greater detail below.

Procedure A

N-[2-(4-Phenylpiperazin-1-yl)-ethyl]-phthalimide 3a

A mixture of 1-phenylpiperazine 2 (2.59 g, 15.98 mmol) was reacted with N-(2-bromoethyl)phthalimide (8.12 g, 31.96 mmol), $Et_3N$ (2.0 mL) and $K_2CO_3$ (8.0 g) in DMF (40 mL) and stirred at 70° C. under $N_2$ overnight. After the reaction mixture was cooled down, water (100 mL) was added. The mixture was extracted with diethyl ether. The organic phase was combined and dried over $Na_2SO_4$. The solvent was removed under vacuo to give the crude product, which was purified by flash chromatography (Hexane/EtOac=1/1) to furnish 3a, 3.81 g (71%) $^1$HNMR ($CDCl_3$) 2.68–2.72 (m, 6H, $N(CH_2)_2$, $CONCH_2$), 3.12–3.15 (t, J=4.8 Hz, 4H, $N(CH_2)_2$), 3.84–3.89 (t, J=6.3 Hz, 2H), 6.80–6.82 (t, J=8.1 Hz, 1H, Ar—H), 6.88–6.91 (d, J=8.1 Hz, 2H, Ar—H), 7.21–7.26 (t, J=8.1 Hz, 2H, Ar—H), 7.69–7.86 (m, 4H, Ar—H).

N-[4-(4-Phenylpiperazin-1-yl)-butyl]-phthalimide 3b

1-Phenylpiperazine 2 (2.21 g, 7.81 mmol) was reacted with N-(4-bromobutyl)phthalimide (1.26 g, 7.81 mmol) in the presence of $K_2CO_3$ (8.0 g) in $Et_3N$ (1.0 mL) and DMF (20 mL) to give a yellow solid 3a, 2.70 (95%) (Procedure A). $^1$H NMR ($CDCl_3$) 1.55–1.82 (m, 4H, $CH_2CH_2$), 2.40–2.45 (t, J=7.5 Hz, 2H, $NCH_2$), 2.57–2.61 (t, J=4.8 Hz, 4H, $N(CH_2)_2$), 3.17–3.20 (t, J=4.8 Hz, 4H, $N(CH_2)_2$), 3.71–3.75 (t, J=6.7 Hz, 2H, $NCH_2$), 6.82–6.94 (3H, Ar—H), 7.23–7.28 (m, 2H, Ar—H), 7.70–7.74 (m, 2H, Ar—H), 7.83–7.86 (m, 2H, Ar—H).

Procedure B 2-(4-Phenylpiperazin-1-yl)-ethylamine 4a

Into the solution of compound 3a (1.97 g, 5.88 mmol) in EtOH (25 mL) was added $NH_2NH_2$ (1.0 g, 31.2 mmol). The reaction mixture was stirred at room temperature under $N_2$ for 24 h. The solvent was removed under vacuo. EtOAc was added. The mixture was filtered and the solution was collected and dried over $Na_2SO_4$. The solvent was removed under vacuo to give a white solid 15, 1.18 g (98%) $^1$HNMR ($CDCl_3$) 2.46–2.51 (t, J=6.3 Hz, 2H, C$H_2$$NH_2$), 2.68–2.71 (t, J=4.8 Hz, 4H, $N(CH_2)_2$), 2.86–2.92 (t, J=6.3 Hz, 2H, $NCH_2$), 3.12–3.16 (t, J=4.8 Hz, 4H, $N(CH_2)_2$), 6.81–6.83 (t, J=8.1 Hz, 1H, Ar—H), 6.88–6.91 (d, J=8.1 Hz, 2H, Ar—H), 7.21–7.26 (t, J=8.1 Hz, 2H, Ar—H).

4-(4-Phenylpiperazin-1-yl)-butylamine 4b

Compound 3b (7.70 g, 21.21 mmol) was reacted with $NH_2NH_2$ (3.0 g, 93.75 mmol) in EtOH (60 mL) to give 4b, 4.60 g (93%) (Procedure B). $^1$H NMR ($CDCl_3$) 1.48–1.61 (m, 4H), 2.83–2.43 (t, J=7.2 Hz, 2H, $NCH_2$), 2.61–2.63 (t, J=4.5 Hz, 4H, $N(CH_2)_2$), 2.72–2.76 (t, J=6.4 Hz, 2H, $NCH_2$), 3.19–3.22 (t, J=4.6 Hz, 4H, $N(CH_2)_2$), 6.33–6.94 (m, 3H, Ar—H), 7.23–7.28 (m, 2H, Ar—H).

Procedure C

7-Methoxyl-2-[(N-(4-phenylpiperazin-1-yl)ethyl)-amino] tetralin 5a

A mixture of compound 4a (1.18 g, 5.75 mmol), 7-methoxyl-tetralone (1.22 g, 6.93 mmol) and $Na(OAc)_3BH$ (3.60 g, 17.26 mmol) in $ClCH_2CH_2Cl$ (20 mL) and HOAc (1.0 mL) was stirred at room temperature under $N_2$ overnight. After the solvent was evaporated, saturated $NaHCO_3$/$H_2O$ (10 mL) was added and the mixture was extracted with EtOAc. The combined organic phase was dried over $Na_2SO_4$ and evaporated to give the crude product, which was purified by flash chromatography (EtOA/MeOH/$Et_3N$=50/5/1) to give solid 5a, 1.95 g (93%). $^1$HNMR ($CDCl_3$) 1.60–1.68 (m, 2H), 2.60–2.63 (m, 6H, $CH_2N$(C$H_2$)$_2$), 2.76–3.04 (m, 7H), 3.16–3.20 (t, J=4.8 Hz, $N(CH_2)_2$), 3.77 (s, 3H, $CH_3O$) 6.62–6.71 (m, 2H, Ar—H), 6.64–7.02 (m, 4H, Ar—H), 7.24–7.30 (m, 2H, Ar—H).

7-Methoxyl-2-[(N-(4-phenylpiperazin-1-yl)-butyl)amino] tetralin 5b 4-(4-Aminobutyl)-1-phenylpiperazine 4 (4.30 g, 18.30 mmol) was reacted with 7-methoxyl-2-tetralone (3.21 g, 18.24 mmol) and $Na(OAc)_3BH$ (11.40 g, 54.03 mmol) in 1,2-dichloroethane (50 mL) and HOAc (1.0 mL) to give a solid 5b 5.80 g (81%) (Procedure C). $^1$H NMR ($CDCl_3$) 1.58–1.60 (m, 4H), 2.03–2.07 (m, 2H), 2.40–2.47 (t, J=6.7 Hz, 2H), 2.59–2.60 (t, J=4.8 Hz, m, 4H, $N(CH_2)_2$), 2.68–2.85 (m, 5H), 2.91–3.03 (m, 2H), 3.19–3.22 (t, J=4.8 Hz, 4H, $N(CH_2)_2$), 3.76 (s, 3H, $CH_3O$), 6.61–6.67 (m, 2H, Ar—H), 6.82–6.97 (m, 4H, Ar—H), 7.23–7.29 (m, 2H, Ar—H). Anal. $C_{25}H_{35}N_3O$ Calcd: C, 76.29; H, 8.95; N, 10.68. Found: C, 76.08; H, 9.00; N, 10.57.

Procedure D

7-Methoxyl-2-[N-butyonitrile-(N-(4-phenylpiperazin-1-yl)-butyl)amino]tetralin 6a A mixture of 5b (1.38 g, 3.51 mmol), 4-bromobutyronitrile (1.39 g, 8.78 mmol), $K_2CO_3$ (5.0 g) and $Et_3N$ (1.0 mL) was stirred in DMF (25 mL) at 60° C. under $N_2$ overnight. The mixture was diluted with water and extracted with diethyl ether. The combined organic phase was dried over $Na_2SO_4$ and evaporated to give crude product, which was purified by flash chromatography (EtOAc/Hexane/$Et_3N$=100/100/1) to give thick oil 6a 1.51 g (93%). $^1H$ NMR (CDCl$_3$) 1.47–1.62 (m, 7H), 1.77–1.81 (t, J=6.6 Hz, 2H, CH$_2$CN), 1.96–2.00 (m, 1H), 2.39–2.44 (t, J=7.2 Hz, 2H, NCH$_2$), 2.44–2.49 (t, J=7.0 Hz, NCH$_2$), 2.52–2.56 (t, 6.8 Hz, 2H, NCH$_2$), 2.61–2.64 (t, J=5.0 Hz, 4H, N(CH$_2$)$_2$), 2.73–2.93 (m, 5H), 3.21–3.24 (t, J=4.8 Hz, 4H, N(CH$_2$)$_2$), 3.77 (s, 3H, CH$_3$O), 6.63–6.71 (m, 2H, Ar—H), 6.84–7.01 (m, 4H, Ar—H), 7.25–7.30 (m, 2H, Ar—H).

7-Methoxyl-2-[N-acetonitrile-(N-(4-phenylpiperazin-1-yl)-butyl)amino]tetralin 6b A mixture of 5b (0.63 g, 1.60 mmol) was reacted with bromoacetonitrile (0.50 g, 4.17 mmol), $K_2CO_3$ (2.20 g) in $Et_3N$ (1.0 mL) and DMF(25 mL) to give a thick oil 6b, 0.53 g (76%) (Procedure D). $^1H$ NMR (CDCl$_3$) 1.52–1.81 (m, 4H), 2.09–2.17 (m, 2H), 2.40–2.44 (t, J=6.3 Hz, 2H), 2.60–2.63 (t, J=4.6 Hz, 4H, N(CH$_2$)$_2$), 2.74–2.88 (m, 5H), 2.89–2.99 (m, 2H), 3.31–3.35 (t, J=4.8 Hz, 4H, N(CH$_2$)$_2$), 3.67 (s, 2H, CH$_2$CN), 3.77 (s, 3H, CH$_3$O), 6.61–6.71 (m, 2H, Ar—H), 6.85–6.97 (m, 4H, Ar—H), 7.24–7.29 (m, 2H, Ar—H).

Procedure E

7-Methoxyl-2-[N-(4-aminobutyl)-(N-(4-phenylpiperazin-1-yl)-butyl)amino]-tetralin 7a Dry THF (5 mL) wad added dropwise into lithium aluminum hydride (LAH) (0.13 g, 3.68 mmol) in ice bath under $N_2$. Compound 6a (0.30 g, 0.65 mmol) in dry THF (15 mL) was added dropwise into above LAH/THF suspension. The reaction mixture was refluxed for 8 h. After the reaction mixture was cooled to room temperature, saturated NaOH/$H_2O$ (1 mL) was added dropwise. The mixture was filtered and the solution was dried over $Na_2SO_4$. The solvent was removed under vacuo to give a white solid 7a, 0.30 g (97%). $^1H$ NMR (CDCl$_3$) 1.56–1.90 (m, 8H), 2.03–2.08 (m, 2H), 2.46–2.51 (t, J=7.2 Hz, 2H), 2.61–2.67 (m, 4H), 2.67–2.70 (t, J=4.8 Hz, 4H, N(CH$_2$)$_2$), 2.77–2.93 (m, 6H); 3.03–3.10 (m, 1H), 3.27–3.30 (t, J=4.8 Hz, 4H, N(CH$_2$)$_2$), 3.77 (s, 3H, CH$_3$O), 6.63–6.70 (m, 2H, Ar—H), 6.83–6.94 (m, 4H, Ar—H), 7.24–7.29(m, 2H, Ar—H).

7-Methoxyl-2-[N-(2-aminoethyl)-(N-(4-phenylpiperazin-1-yl)-butyl)amino]-tetralin 7b Compound 6b (0.37 g, 0.86 mmol) was reacted with LAH (0.23 g, 7.60 mmol) in dry THF (20 mL) to give a white solid 7b, 0.35 g (95%) (Procedure E). $^1H$ NMR (CDCl$_3$) 1.54–1.65 (m, 4H), 2.09–2.13 (m, 2H), 2.39–2.44 (t, J=7.2 Hz, 2H), 2.59–2.63 (m, J=4.5 Hz, 4H, N(CH$_2$)$_2$), 2.74–2.89 (m, 10H), 3.02–3.06 (m, 1H), 3.19–3.22 (t, J=4.8 HZ, 4H, N(CH$_2$)$_2$), 3.77 (s, 3H, CH$_3$O), 6.63–6.71 (m, 2H, Ar—H), 6.83–6.92 (m, 4H, Ar—H), 7.25–7.30 (m, 2H, Ar—H).

Procedure F

7-Hydroxyl-2-[N-butyonitrile-(N-(4-phenylpiperazin-1-yl)-butyl)amino]tetralin 8

Compound 6a (0.29 g, 0.63 mmol) was dissolved in dry $CH_2Cl_2$ (10 mL). The solution was cooled to −40° C. by dry ice. The solution of 1M $BBr_3$/$CH_2Cl_2$ (1.0 mL) was added slowly. The reaction mixture was stirred at −40° C. for 2 h and then at room temperature overnight. Saturated $NaHCO_3$/$H_2O$ was added and the mixture was extracted by $CH_2Cl_2$. The combined organic phase was dried over $Na_2SO_4$. After the solvent was removed under vacuo, the crude product was purified with flash chromatography (EtOAc/$Et_3N$=50/1) to give compound 8, 0.18 g (65%). $^1H$ NMR (CDCl$_3$) 1.47–1.61 (m, 8H), 1.75–1.79 (t, J=6.6 Hz, 2H, CH$_2$CN), 1.94–1.97 (m, 2H), 2.39–2.47 (m, 4H), 2.49–2.54 (t, J=6.3 Hz, 2H, NCH$_2$), 2.61–2.64 (t, J=5.1 Hz, 4H, N(CH$_2$)$_2$), 2.69–2.91 (m, 5H), 3.20–3.23 (t, J=4.5 Hz, 4H, N(CH$_2$)$_2$), 6.54–6.60 (m, 2H, Ar—H), 6.83–6.95 (m, 3H, Ar—H), 7.24–7.29 (m, 2H, Ar—H). Free base was converted into its HBr salt. m.p.=171–175° C. Anal. ($C_{28}H_{38}N_4O$.3 HBr) Cacl: C, 49.94; H, 6.14; N, 8.32; Found: C, 49.94; H, 6.28; N, 8.29.

Procedure G

7-Methoxyl-2-[N-(4-benzoylaminobutyl)-(N-(4-phenylpiperazin-1-yl)-butyl)amino]tetralin 9a Benzoic acid (0.10 g, 0.78 mmol), 1-[3-(dimethylamino)propyl]-3-ethylcarbodiimide hydrochloride (0.14 g, 0.71 mmol) and 1-hydroxybenzotriazole (0.11 g, 0.78 mmol) were dissolved in dry $CH_2Cl_2$ (10 mL). The solution was stirred at room temperature for 0.5 h. 7a (0.30 g, 0.65 mmol) in $CH_2Cl_2$ (10 mL) was added into the above solution. The reaction mixture was stirred at room temperature overnight. The solvent was evaporated and $H_2O$ (50 mL) was added. The mixture was extracted with EtOAc. The organic phase was dried over $Na_2SO_4$. After evaporation, the crude product was purified with flash chromatography (EtOAc/$Et_3N$=50/1) to give compound 9, 0.26 g (71%). $^1H$ NMR (CDCl$_3$) 1.52–1.67 (m, 8H), 1.97–2.05 (m, 2H), 2.36–2.41 (t, J=6.9 Hz, 2H), 2.59–2.62 (t, J=4.8 Hz, 6H, N(CH$_2$)$_2$, NCH$_2$), 2.74–2.87 (m, 4H), 2.97–3.07 (m, 1H), 3.18–3.22 (t, J=4.8 Hz, N(CH$_2$)$_2$), 3.46–3.52 (t, J=6.2 Hz, 2H), 3.71(s, 3H, CH$_3$O), 6.57–6.71 (m, 2H), 6.84–7.00 (m, 4H, Ar—H), 7.25–7.27 (m, 2H, Ar—H), 7.40–7.52 (m, 3H, Ar—H), 7.77–7.79 (d, J=7.9 Hz, 2H).

7-Methoxyl-2-[N-(2-benzoylamino)ethyl-(N-(4-phenylpiperazin-1-yl)-butyl)amino]tetralin 9b Compound 7b (0.35 g, 0.84 mmol) was reacted with benzoic acid (0.12 g, 1.02 mmol), 1-[3-(dimethylamino)propyl]-3-ethylcarbodiimide-hydrochloride (0.19 g, 0.10 mmol) and 1-hydroxybenzotriazole (0.14 g, 1.01 mmol) in $CH_2Cl_2$ (20 mL) to give compound 9b, 0.30 g (69%) (Procedue G). $^1H$ NMR(CDCl$_3$) 1.53–1.61 (m, 4H), 1.97–2.05 (m, 2H), 2.34–2.38 (t, J=6.2 Hz, 2H), 2.53–2.42 (t, J=4.2 Hz, 4H, N(CH$_2$)$_2$), 2.59–2.62 (m, 2H), 2.73–2.81 (m, 6H), 3.03–3.05 (m, 1H), 3.13–3.16 (t, J=4.5 Hz, 4H, N(CH$_2$)$_2$), 3.48–3.52 (m, 2H), 3.76(s, 3H, CH$_3$O), 6.59–6.68 (m, 2H, Ar—H), 6.85–7.00 (m, 4H, Ar—H), 7.24–7.28 (m, 2H, Ar—H), 7.42–7.51 (m, 3H, Ar—H), 7.78–7.80 (d, J=6.9 Hz, 2H, Ar—H).

7-Hydroxyl-2-[N-(4-benzoylaminobutyl)-(N-(4-phenylpiperazin-1-yl)-butyl)amino]tetralin 10a Compound 9a (0.17 g, 0.30 mmol) was reacted with 1.0 M $BBr_3$/$CH_2Cl_2$ (1.5 mL) to give compound 10a, 0.12 g (72%) (Procedure F). m.p.=70–71° C. $^1H$ NMR (CDCl$_3$) 1.52–1.69 (m, 8H), 1.97–2.05 (m, 2H), NCH$_2$), 2.54–2.61 (m, 6H, N(CH$_2$)$_2$), 2.71–2.84 (m, 4H), 2.36–2.41(t, J=6.9 Hz, 2H), 2.95–3.05(m, 1H, NCH), 3.18–3.21(t, J=4.6 Hz, 4H, N(CH$_2$)$_2$), 3.45–3.51 (t J=6.2 Hz, 2H), 6.52–6.61(m, Ar—H, 2H), 6.83–6.88(m, 4H, Ar—H), 7.24–7.29 (m, 2H, Ar—H), 7.39–7.49 (m, 3H, Ar—H), 7.76–7.79(d, J=7.2 Hz, 2H, Ar—H) Anal. $C_{35}H_{46}N_4O_2$.0.22$H_2O$, Cacl: C, 75.26; H, 8.37; N, 10.01; Found: C, 75.23; H, 8.28; N, 9.75.

7-Hydroxyl-2-[N-(2-benzoylamino)ethyl-(N-(4-phenylpiperazin-1-yl)-butyl]amino]tetralin 10b Compound 9b (0.28 g, 0.53 mmol) was reacted with 1M BBr$_3$/CH$_2$Cl$_2$ (2.0 mL, 2.0 mmol) to give compound 10b, 0.21 g(76%) (Procedure F). m.p.=68–69° C. $^1$H NMR (CDCl$_3$) 1.54–1.70 (m, 4H), 1.89–2.05 (m, 2H), 2.35–2.39 (t, J=4.9 Hz, 2H), 2.53–2.56 (t, J=4.2 Hz, 4H, N(CH$_2$)$_2$), 2.61–2.67 (m, 2H), 2.72–2.98 (m, 6H), 2.99–3.07 (m, 2H), 3.14–3.17 (t, J=4.5 Hz, 4H, N(CH2)2), 3.45–3.53 (m, 2H), 6.51–6.61 (m, 2H, Ar—H), 6.86–6.92 (m, 4H, Ar—H), 7.24–7.29 (m, 2H, Ar—H), 7.42–7.51 (m, 3H, Ar—H), 7.79–7.81(d, J=6.9 Hz, 2H, Ar—H). Anal. (C$_{35}$H$_{48}$N$_4$O$_2$.0.22H$_2$O) Cacl: C, 74.75; H, 8.05; N, 10.56; sound, C, H, 8.22; N, 10.03.

7-Methoxyl-2-[N-propargyl-(N-(4-phenylpiperazin-1-yl)-ethyl)amino]tetralin 11a Compound 5a (1.18 g, 3.04 mmol) was reacted with propargyl chloride (1.20 g, 16.11 mmol) in the presence of K$_2$CO$_3$ (4.0 g) and DMF (25 mL) at 60° C. for 5 h to furnish 11a, 0.35 g (29%) (Procedure D). $^1$HNMR (CDCl$_3$) 1.59–1.71 (m, 2H), 2.13–2.18 (m, 2H), 2.20–2.34 (t, J=2.1 Hz, 1H, C≡CH), 2.56–2.60 (t, J=6.9 Hz, 2H, NCH$_2$), 2.65–2.68 (t, J=4.8 Hz, 4H, N(CH$_2$)$_2$), 2.75–2.81 (m, 2H), 2.84–2.89 (t, J=7.2 Hz, 2H), 2.98–3.02 (m, 3H), 3.20–3.23 (t, J=4.8 Hz, 4H, N(CH$_2$)$_2$), 3.60 (s, 2H, NCH$_2$C≡CH), 3.77 (s, 3H, CH$_3$O), 6.60–6.83 (m, 2H, Ar—H), 6.85–6.98 (m, 4H, Ar—H), 7.23–7.29 (m, 2H, Ar—H).

7-Methoxyl-2-[N-propargyl-(N-(4-phenylpiperazin-1-yl)-butyl)amino]tetralin 11b A mixture of 5b (0.65 g, 1.65 mmol), propargyl chloride (0.30 mL, 4.63 mmol), K$_2$CO$_3$ (1.0 g) and Et$_3$N (1.0 mL) was stirred in DMF (20 mL) at 60° C. under N$_2$ for 5 h to give a thick oil 11b, 0.33 g (46%) (Procedure D). $^1$H NMR (CDCl$_3$) 1.51–1.56 (m, 4H), 2.11–2.15 (m, 2H), 2.17–2.19 (t, J=2.2 HZ, 1H, C≡CH), 2.40–2.44 (t, J=7.2 Hz, 2H), 2.59–2.63 (t, J=4.8 Hz, 4H, N(CH$_2$)$_2$), 2.67–2.83 (m, 5H), 2.93–3.01 (m, 2H), 3.19–3.23 (t, J=4.5 HZ, 4H, N(CH$_2$)$_2$), 3.52–3.53 (d, J=2.1 Hz, 2H, CH$_2$C≡CH), 3.77 (s, 3H, CH$_3$O), 6.62–6.70 (m, 2H, Ar—H), 6.83–7.00 (m, 4H, Ar—H), 7.24–7.29 (m, 2H, Ar—H).

7-Hydroxyl-2-[N-propargyl-(N-(4-phenylpiperazin-1-yl)-ethyl)amino]tetralin 12a Compound 11a (0.28 g, 0.70 mmol) was reacted with 1M BBr$_3$/CH$_2$Cl$_2$ (1.50 mL, 1.50 mmol) in CH$_2$Cl$_2$ (15 mL) to furnish 12a, 0.23 g (84%) (Procedure E). $^1$HNMR (CDCl$_3$) 1.56–1.68 (m, 2H), 2.11–2.15 (m, 2H), 2.20–2.22 (t, J=2.1 Hz, 1H, C≡CH), 2.57–2.61 (t, J=6.6 Hz, 2H, NCH$_2$), 2.65–2.69 (t, J=4.8 Hz, 4H, N(CH$_2$)$_2$), 2.75–2.81 (m, 2H), 2.86–2.91 (t, J=4.8 Hz, 2H, N(CH$_2$)$_2$), 3.58 (s, 2H, CH$_2$C≡CH), 6.55–6.61 (m, 2H, Ar—H), 6.83–6.94 (m, 4H, Ar—H). 7.23–7.27 (m, 2H, Ar—H). Free base was converted into its HCl salt. m.p.=164–166° C. Anal. (C$_{27}$H$_{31}$N$_3$O.3HCl.0.8H$_2$O) Calcd. C, 58.49; H, 6.98; N 8.18; Found: C, 58.58; H, 6.77; N, 8.05.

7-Hydroxyl-2-[N-propargyl-(N-(4-phenylpiperazin-1-yl)-butyl)amino]tetralin 12b Compound 11b (0.195 g, 0.742 mmol) was reacted with 1M BBr$_3$/CH$_2$Cl$_2$ (0.80 mL, 0.80 mmol) to give compound 12b, 0.13 g (72%). $^1$HNMR (CDCl$_3$) 1.54–1.68 (m, 4H), 2.09–2.14 (m, 2H), 2.17–2.18 (t, J=2.1 Hz, 1H), 2.41–2.45 (t, J=7.0 Hz, 2H), 2.60–2.63 (t, J=4.5 Hz, 4H, N(CH$_2$)$_2$), 2.67–2.71 (t, J=6.2 Hz, 2H), 2.76–2.80 (m, 3H), 2.89–2.92 (m, 1H) 3.51–3.52 (d, J=2.1 Hz, 2H, CH$_2$C≡CH), 3.20–3.24 (t, J=4.6 Hz, 4H, N(CH$_2$)$_2$), 6.56–6.61 (m, 2H, Ar—H), 6.88–6.95 (m, 4H, Ar—H), 7.24–7.29 (m, 2H, Ar—H),). Free base was converted into its HBr salt. m.p.= 182–186° C. Anal. (C$_{27}$H$_{35}$N$_3$O.3HBr.0.75H$_2$O). Cacl: C, 48.12; H, 5.87; N, 6.24; Found: C, 48.12; H, 5.86; N, 6.20.

Procedure H
7-Methoxyl-2-[N-propionyl-(N-(4-phenylpiperazin-1-yl)-ethyl)amino]tetralin 13a Compound 5a (0.36 g, 0.97 mmol) was dissolved in CH$_2$Cl$_2$ (10 mL) and Et$_3$N (1.0 mL). The solution was cooled in an ice bath, and propionyl chloride (0.20 g, 2.16 mmol) was added. After the reaction mixture was stirred at room, temperature for 2 h, TLC showed completion of the reaction. The solvent was removed under vacuo. The mixture was dissolved in EtOAc and washed with H$_2$O. The organic phase was dried over Na$_2$SO$_4$. The evaporation of the solution gave the crude product, which was purified by flash chromatography (EtOAc/MeOH/Et$_3$N=95/5/0.5) to give 13a, 0.42 g (93%) (Procedure F). $^1$HNMR (CDCl$_3$) 1.14–1.20 (t, J=6.6 Hz, 3H, CH$_3$CH$_2$CO), 1.63–1.70 (m, 2H), 1.90–2.04 (m, 2H), 2.40–2.50 (m, 4H), 2.66–2.74 (t, J=4.8 Hz, 4H, N(CH$_2$)$_2$) 2.76–2.91 (m, 5H), 3.20–3.22 (t, J=4.8 Hz, 4H, N(CH$_2$)$_2$), 3.78 (s, 3H, CH$_3$O), 6.60–6.70 (m, 2H, Ar—H), 6.91–7.01 (m, 4H, Ar—H), 7.25–7.29 (m, 2H, Ar—H).

7-Methoxyl-2-[N-propionyl-(N-(4-phenylpiperazin-1-yl)-butyl)amino]tetralin 13b Compound 5b (0.28 g, 0.71 mmol) was reacted with propionyl chloride (0.25 g, 3.57 mmol) in CH$_2$Cl$_2$ (10 mL) and Et$_3$N (1.0 mL) to give pure compound 18, 0.32 g (99%). $^1$H NMR (CDCl$_3$) 1.11–1.26 (t, J=6.6 Hz, 3H), 1.52–1.74 (m, 5H), 1.89–1.98 (m, 1H), 2.35–2.45(m, 4H), 2.58–2.61 (t, J=4.5 Hz, 4H, N(CH$_2$)$_2$), 2.78–3.05 (m, 4H), 3.18–3.23 (t, J=4.5 Hz, 4H, N(CH$_2$)$_2$), 3.15–3.56 (m, 1H), 3.76 (s, 3H, CH$_3$O—), 6.58–6.73 (m, 2H, Ar—H), 6.85–7.03 (m, 4H, Ar—H), 7.23–7.28 (t, J=7.6 Hz, 2H, Ar—H).

7-Methoxyl-2-[N-propyl-(N-(4-phenylpiperazin-1-yl)-ethyl)amino]tetralin 14a

Compound 13a (0.38 g, 0.90 mmol) was reacted with LAH (0.15 g, 4.41 mmol) in THF (25 mL) to furnish 14a, 0.36 g (97%) (procedure E). $^1$HNMR (CDCl$_3$) 0.87–0.93 (t, J=7.2 Hz, 3H, CH$_3$CH$_2$CH$_2$N), 1.46–1.53 (m, 4H), 1.88–2.07 (m, 2H), 2.51–2.55 (t, J=7.2 Hz, 2H, CH$_2$N), 2.64–2.68 (t, J=4.8 Hz, 4H, N(CH$_2$)$_2$), 2.72–2.83 (m, 6H), 2.90–3.06 (m, 1H), 3.19–3.22 (t, J=4.8 Hz, 4H, N(CH$_2$)$_2$), 3.77 (s, 3H, CH$_3$O), 6.62–6.70 (m, 2H, Ar—H), 6.85–7.00 (m, 4H, Ar—H), 7.24–7.29 (m, 2H, Ar—H).

7-Methoxyl-2-[N-propyl-(N-(4-phenylpiperazin-1-yl)-butyl)amino]tetralin 14b

Compound 13b (0.30 g, 0.71 mmol) was reacted with LAH (0.25 g, 7.57 mmol) in THF (20 mL) to give 14b 0.28 g (99%) (procedure E). $^1$H NMR (CDCl$_3$) 0.86–0.91 (t, J=7.2 Hz, 3H), 1.40–1.66 (m, 7H), 1.98–2.05 (m, 1H), 2.38–2.43 (t, J=7.2 Hz, 2H), 2.45–2.50 (t, J=7.2 Hz, 2H), 2.52–2.56 (t, J=6.8 Hz, 2H), 2.59–2.62 (t, J=4.8 Hz, 4H, N(CH$_2$)$_2$), 2.69–2.88 (m, 4H), 2.91–3.02 (m, 1H), 3.20–3.22 (t, J=4.5 Hz, 4H, N(CH$_2$)$_2$), 3.77 (s, 3H, CH$_3$O), 6.62–6.69 (m, 2H, Ar—H), 6.83–7.00 (m, 4H, Ar—H), 7.24–7.29 (m, 2H, Ar—H).

7-Hydroxyl-2-[N-propyl-(N-(4-phenylpiperazin-1-yl)-ethyl)amino]tetralin 15a

Compound 14a (0.60 g, 0.88 mmol) was reacted with 1M BBr$_3$/CH$_2$Cl$_2$ (1.60 mL, 1.60 mmol) in CH$_2$Cl$_2$ (20 mL) to furnish 15a, 0.29 g (83%) (Procedure F). $^1$H NMR (CDCl$_3$) 0.86–0.91 (t, J=7.2 Hz, 3H, CH$_3$CH$_2$CH$_2$N), 1.43–1.50 (m, 4H), 1.89–1.93 (m, 2H), 2.46–2.51 (t, J=7.5 Hz, 2H, NCH$_2$), 2.53–2.68 (m, 6H), 2.70–2.74 (t, J=4.8 Hz, 4HN(CH$_2$)$_2$), 2.83–2.88 (m, 1H), 3.23–3.26 (t, J=4.8 Hz, 4H, N(CH$_2$)$_2$), 6.45–6.56 (m, 2H, Ar—H), 6.83–6.93 (m, 4H, Ar—H), 7.23–7.26 (m, 2H, Ar—H). Free base was converted into its HCl salt, m.p.=143–146° C. Anal. (C$_{27}$H$_{35}$N$_3$O.3HCl.0.9H$_2$O) Calcd. C, 57.83; H, 7.72; N, 8.09; Found: C, 57.88; H, 7.52; N, 7.90.

7-Hydroxyl-2-[N-propyl-(N-(4-phenylpiperazin-1-yl)-butyl)amino]tetralin 15b

Compound 19 (0.30 g, 0.69 mmol) was reacted with 1M BBr$_3$/CH$_2$Cl$_2$ (1.3 mL) to give 20, 0.25 g (87%) (Procedure F). $^1$H NMR (CDCl$_3$) 0.86–0.91 (t, J=7.2 Hz, 3H), 1.40–1.82 (m, 7H), 1.93–2.05 (m, 1H), 2.39–2.39–2.44 (t, J=7.2 Hz, 2H), 2.44–2.50 (t, J=7.5 Hz, 2H), 2.56–2.51(t, J=6.6 Hz, 2H), 2.60–2.63 (t, J=4.2 Hz, 4H, N(CH$_2$)$_2$), 2.75–2.80 (m, 4H), 2.92–2.99 (m, 1H), 3.20–3.23 (t, J=4.2 Hz, 4H, N(CH$_2$)$_2$), 6.54–6.60 (m, 2H, Ar—H), 6.83–6.95 (m, 4H, Ar—H), 7.24–7.29 (m, 2H, Ar—H). Free base was converted into its HBr salt. m.p.=152–156° C. Anal. C$_{27}$H$_{42}$N$_3$OBr$_3$.0.30H$_2$O. Cacl: C, 48.42; H, 6.41; N, 6.27. Found: C, 48.10; H, 6.64; N, 6.11.

7-Methoxyl-2-[(N-(4-(2,3-dichlorophenyl)-piperazin-1-yl)-butyl)amino]tetralin 17

Compound 17 was synthesized from 16 according to the procedures (A, B and C) (70%, 3 steps). $^1$HNMR (CDCl$_3$) 1.58–1.64 (m, 4H), 2.04–2.10 (m, 2H), 2.43–2.47 (t, J=6.6 Hz, 2H), 2.60–2.65 (m, 4H N(CH$_2$)$_2$), 2.76–2.82 (m, 5H), 2.93–2.98 (m, 2H), 3.02–3.08 (m, 4H, N(CH$_2$)$_2$), 3.77 (s, 3H, CH$_3$O), 6.62–6.71 (m, 2H, Ar—H), 6.94–7.01 (m, 2H, Ar—H), 7.14–7.16 (m, 2H, Ar—H).

7-Methoxyl-2-[N-propanyl-(N-(4-(2,3-dichlorophenyl)-piperazin-1-yl)-butyl)amino]tetralin 18a Compound 18a was synthesized from 17 according to the procedure (H, E) in (92%, two steps). $^1$HNMR (CDCl$_3$) 0.89–0.93 (t, J=7.2 Hz, 3H, CH$_3$CH$_2$), 1.47–1.61 (m, 6H), 2.02–2.05 (m, 2H), 2.44–2.49 (t, J=7.2 Hz, 2H, NCH$_2$), 2.52–2.65 (m, 8H), 2.76–2.87 (m, 5H), 3.07–3.08 (bs, 4H, N(CH$_2$)$_2$), 3.77 (s, 3H, CH$_3$O), 6.63–6.70 (m, 2H, Ar—H), 6.95–7.00 (m, 2H, Ar—H), 7.14–7.19 (t, J=2.7 Hz, 2H, Ar—H).

7-Methoxyl-2-[N-propargyl-(N-(4-(2,3-dichlorophenyl)-piperazin-1-yl)-butyl)amino]tetralin 18b Compound 17 was reacted with propargyl chloride (1.50 g, 20.13 mmol) and K$_2$CO$_3$ (4.50 g) in DMF (20 mL) to give 18b, 0.48 g (24%). $^1$HNMR (CDCl$_3$) 1.55–1.68 (m, 4H), 2.11–2.15 (m, 2H), 2.17–2.18 (t, J=1.8 Hz, 1H, C≡CH), 2.43–2.47 (t, J=6.6 Hz, 2H), 2.49–2.66 (bs, 4H, N(CH$_2$)$_2$), 2.68–2.88 (m, 8H), 2.98–3.00 (m, 1H), 3.06–3.10 (bs, 4H, N(CH$_2$)$_2$), 3.52–3.53 (d, J=1.8 Hz, 2H, CH2C≡CH), 3.77 (s, 3H, CH$_3$O), 6.30–6.72 (m, 2H, Ar—H), 6.94–7.00 (m, 2H, Ar—H), 6.97–7.16 (m, 2H, Ar—H).

7-Hydroxyl-2-[N-propyl-(N-(4-(2,3-dichlorophenyl)-piperazin-1-yl)-butyl)amino]tetralin 19a Compound 10 (0.36 g, 0.71 mmol) was reacted with 1M BBr$_3$/CH$_2$Cl$_2$ (1.5 mL, 1.5 mmol) to give product 11 (0.29 g, 83%). $^1$HNMR (CDCl$_3$) 0.85–0.90 (t, J=7.2Hz, 3H, CH$_3$), 1.43–1.58 (m, 6H), 1.96–2.00 (m, 2H), 2.44–2.55 (m, 6H, CH$_2$NN(CH$_2$)$_2$), 2.69–2.77 (m, 8H), 2.94–2.95 (m, 1H), 3.08–3.09 (bs, 4H, N(CH$_2$)$_2$), 6.51–6.57 (m, 2H, Ar—H), 6.88–6.93 (m, 2H, Ar—H), 7.09–7.15 (m, 2H, Ar—H). Free base was converted into its HCl salt, m.p.=155–159° C. Anal. Calcd. (C$_{27}$H$_{37}$N$_3$OCl$_2$.3HCl.0.8H$_2$O) C, 52.79; H, 6.82; N, 6.84; Found: C, 52.50; H, 6.82; N, 6.84.

7-Hydroxyl-2-[N-propargyl-(N-(4-(2,3-dichlorophenyl)-piperazin-1-yl)-butyl)amino]tetralin 19b Compound 18b (0.28 g, 0.70 mmol was reacted with 1M BBr$_3$/CH$_2$Cl$_2$ (1.50 mL, 1.50 mmol) to give pure product 8, 0.23 g (84%). $^1$HNMR (CDCl$_3$) 1.48–1.56 (m, 4H), 2.09–2.13 (m, 2H), 2.17–2.18 (t, J=1.8 Hz, 1H, C≡CH), 2.45–2.47 (t, J=6.6 Hz, 2H), 2.66–2.68 (bs, 4H, N(CH$_2$)$_2$), 2.71–2.80 (m, 5H), 2.89–2.96 (m, 2H), 3.09–3.10 (bs, 4H, N(CH$_2$)$_2$), 3.51–3.52 (d, J=1.5Hz, 2H, CH$_2$C≡CH), 6.57–6.61 (m, 2H, Ar—H), 6.92–6.98 (m, 2H, Ar—H), 7.14–7.16 (m, 2H, Ar—H). Free base was converted into its HCl salt, m.p.=180–183° C. Anal. Calcd. (C$_{27}$H$_{33}$N$_3$OCl$_2$.2.70HCl.0.06H$_2$O) C, 55.34; H, 6.16; N, 7.18; Found: H, 6.16; N, 7.10.

4-[N-(4-phenylpiperazin-1-yl)-ethylamino]-cyclohexanone ethylene ketal 20

A mixture of amine 4a (2.21 g, 10.8 mmol), ketone (1.68 g, 10.8 mol) and Na(OAc)$_3$BH (3.24 g, 15.12 mmol) in HOAc(0.65 g, 10.8 mol) and ClCH$_2$CH$_2$Cl (40 mL) was stirred at room temperature for overnight. The reaction mixture was diluted with EtOAc(200 mL), washed with brine, and dried over Na$_2$SO$_4$. After the evaporation of the organic layer, the crude product was purified by flash chromatography(EtOAc/MeOH/Et$_3$N=100/5/1) to give white solid 20, 3.55 g (91%). $^1$H NMR (300 MHz, CD$_3$Cl) 1.52–1.56(m, 6H), 1.74–1.79(m, 2H), 1.91–1.96(m, 2H), 2.57–2.66(m, 7H, N(CH$_2$)$_2$, CHNHCH$_2$), 2.80–2.84(t, J=6.0 Hz, 2H), 3.14–3.18(t, J=48 Hz, 4H, N(CH$_2$)$_2$), 3.90(s, 4H, OCH$_2$CH$_2$O), 6.83–6.91(m, 3H, Ar—H), 7.21–7.25(m, 2H, Ar—H).

4-[N-propyl-(N-(4-phenylpiperazin-1-yl)-ethyl)amino]-cyclohexanone ethylene ketal 21

A mixture of amine 20 (1.0 g, 2.94 mmol), 1-bromopropane (1.45 g, 11.80 mol) and K$_2$CO$_3$ (1.22 g, 8.70 mmol) in dry DMF(20 mL) was stirred at 60° C. for 10 h. The mixture was poured into water(50 mL) and extracted with Et$_2$O (3×100 mL). The combined organic layer was washed with brine and dried over Na$_2$SO$_4$. After the evaporation of the organic solvent, the residue was purified by flash chromatography(EtOAc/MeOH/Et$_3$N=100/2/1) to give a thick oil 21 0.80 g (70%). $^1$H NMR(300 MHz, CD$_3$Cl) 0.83–0.88 (t, J=7.2 Hz, 3H, CH$_3$), 1.40–1.47(m, 2H), 1.52–1.58(m, 4H), 1.73–1.80(m, 4H), 2.41–2.50(m, 4H), 2.58–2.65(m, 7H), 3.17–3,20(t, J=5.2 Hz, 4H, N(CH$_2$)$_2$), 3.17–3.20(t, J=5.2 Hz, 4H, N(CH$_2$)$_2$), 3.92(s, 4H, OCH$_2$CH$_2$O), 6.82–6.86(t, J=7.2 Hz, 1H, Ar—H), 6.90–6.93(d, J=7.8 Hz, 2H, Ar—H), 7.22–7.28(m, 2H, Ar—H).

4-[N-propyl-(N-(4-phenylpiperazin-1-yl)-ethyl)amino]-cyclohexanone 22

A solution of ketal 21 (2.00 g, 5.17 mmol) in THF (20 mL) and 1N HCl(20 mL) was stirred at 80° C. under N$_2$ for 2 h. THF was removed under vacuo and solid NaHCO$_3$ was added slowly extracted with EtOAc(3×100 mL). The combined organic layer was washed with brine and dried over Na$_2$SO$_4$. The evaporation gave the crude product, which was purified by flash chromatography(EtOAc/Et$_3$N=100/1) to give 22, 1.31 g(99%). $^1$H NMR (300 MHz, CD$_3$Cl) 0.87–0.90(t, J=5.7 Hz, 3H, CH$_3$), 1.43–1.51(dt, J=5.7, 6.0 Hz, 2H, NCH$_2$CH$_2$CH$_3$), 1.70–1.79(m, 2H), 2.04–2.07(m, 2H), 2.30–2.52(m, 8H), 2.64–2.70(m, 6H), 2.97–3.03(t, J=10.4 Hz, 1H, NCH(CH$_2$)$_2$), 3.19–3.21(t, J=4.4 Hz, 4H, N(CH$_2$)$_2$), 6.83–6.87(t, J=7.2 Hz, 1H, Ar—H), 6.91–6.93(d, J=8.0 Hz, 2H, Ar—H), 7.24–7.28(m, 2H, Ar—H).

2-Amino-6-[N-propyl-(N-(4-phenylpiperazin-1-yl)-ethyl) amino]-5,6,7,8-tetrahydrobenzopyrimidine 23

To a solution of ketone 22 (0.60 g, 1.75 mmol) in dry toluene(20 mL) was added tris(dimethylamino)methane (1.27 g, 8.76 mmol), and the mixture stirred under nitrogen at 90° C. for 4 h. The solvent was removed under vacuo, and the residue was dissolved in EtOH (25 mL). Guandine carbonate (0.78 g, 4.33 mmol) was added, and the mixture was held at reflux for 17 h. The solvent was evaporated, and the residue diluted with CH$_2$Cl$_2$ and washed with brine. The organic layer was dried over Na$_2$SO$_4$ and evaporated to give the crude product, which was purified by flash chromatography (EtOAc/MeOH/Et$_3$N=25/1/1) to give a yellow solid 23, 0.61 g(88%). $^1$H NMR(300 MHz, CD$_3$Cl) 0.86–0.91(t, J=7.2 Hz, 3H, CH$_3$), 1.44–1.52(dt, J=7.2, 7.2 Hz, 2H, NCH$_2$CH$_2$CH$_3$), 1.61–1.74(m, 1H), 2.03–2.10(m, 1H), 2.49–2.56 (m, 4H), 2.64–2.67(t, J=5.0 Hz, 4H, N(CH$_2$)$_2$), 2.69–2.75(m, 4H), 2.79–2.81(dd, J=2.8, 6.0 Hz, 1H), 2.85–2.95(m, 1H), 3.18–3.21(t, J=5.0 Hz, 4H, N(CH$_2$)$_2$), 4.88(s, 2H, NH$_2$), 6.82–6.87(t, J=7.2 Hz, 1H, Ar—H), 6.90–6.93(d, J=8.4 Hz, 2H, Ar—H), 8.01(s, 1H, H-pyrimidine). Free base was converted into HCl salt. m.p.=97–102° C. Anal: (C$_{23}$H$_{34}$N$_6$.5HCl.0.2H$_2$O) Cacl: C, 47.90, H, 6.85, N, 14.47; Found: C, 48.36, H, 7.38, N, 14.48.

2-Bromo-4-[N-propyl-(N-(4-phenylpiperazin-1-yl)-ethyl)amino]-cyclohexanone 24

Into the solution of ketone 22 (0.86, 2.51 mmol) in HOAc (50 mL) and 40% HBr/HOAc(w/v) (3.0 mL) was added Bromine (0.45 g, 2.81 mmol) in HOAc(10 mL) dropwise. The white solid was precipitated after several minutes. The mixture was stirred for 1 h and the most of solvent was removed under vacuo. The solid was collected with filtration and dried under vacuo to give 1.45 g(87%).

2-Amino-5-[N-propyl-(N-(4-phenylpiperazin-1-yl)-ethyl)amino]-4,5,6,7-tetrahydrobenzothiazole 25

A solution of bromide HBr salt 24 (0.99 g, 1.49 mmol), thiourea (0.14 g, 179 mmol) in EtOH (50 mL) was refluxed for 2 h. The solvent was removed under vacuo. The residue was diluted with EtOAc and solid NaHCO$_3$ was added. The mixture was filtered and the organic layer was evaporated to give crude product, which was purified with flash chromatography (EtOAc/Et$_3$N=100/1) to give pure compound 25, 140 mg. $^1$H NMR(300 MHz, CD$_3$Cl)0.87–0.91(t, J=8.0 Hz, 3H, CH$_3$), 1.43–1.52(h, J=7.2 Hz, 2H, CH$_3$CH$_2$CH$_2$N), 1.69–1.79(dq, J=4.8, 12.8 Hz, 2H), 1.86(bs, 2H, NH2), 2.04–2.30(m, 2H), 2.30–2.38(dt, J=6.0, 13.6 Hz, 2H), 2.42–2.52(m, 6H), 2.64–7.71(m, 6H), 2.97–3.03(dt, J=3.4, 8.0 Hz, 1H), 3.19–3.21(t, J=5.2 Hz, 4H, N(CH$_2$)$_2$), 6.83–6.87(t, J=7.2 Hz, 1H, Ar—H), 6.91–6.93(d, J=8.0 Hz, 2H, Ar—H), 7.24–7.28(m, 2H, Ar—H).

2-(4-Nitro-phenyl)-N-[2-(4-phenyl-piperazin-1-yl)-ethyl]-acetamide (26a)

To a stirred solution of 2-(4-Phenyl-piperazin-1-yl)-ethylamine 4a (0.5 g, 2.44 mmol) and Et$_3$N (0.34 g, 3.41 mmol) in 40 mL of dry CH$_2$Cl$_2$ under nitrogen at 0° C. was added a solution (4-Nitro-phenyl)-acetyl chloride (0.58 g, 2.92 mmol). The temperature was allowed to rise to room temperature, the mixture was stirred for 2 h, and then washed with water. The aqueous layer was extracted with dichloromethane. The combined organic phase was washed with saturated sodium chloride, dried (Na$_2$SO$_4$) and concentrated. The crude product was purified by column chromatography over silica gel (EtOAc) to produce 26a: 0.8 g, (89% yield) as a white solid (mp: 138–139° C.). $^1$H NMR (CDCl$_3$, 400 MHz): δ2.52 (2H, t, J=5.6, CH$_2$—CH$_2$NH), 2.57 (4H, t, J=5.2, (CH$_2$)$_2$N—), 3.11 (4H, t, J=5.2, (CH$_2$)$_2$—NPh), 3.36–3.34 (2H, m, CH$_2$—NHCO), 3.65 (2H, s, CH$_2$Ar), 6.19 (1H, bs, NHCO), 6.86–6.91(3H, m, ArH), 7.25–7.29 (2H, m, ArH), 7.47 (2H, d, J=8.8, ArH), 8.16–8.19 (2H, m, ArH).

2-(3-nitro-phenyl)-N-[2-(4-phenyl-piperazin-1-yl)-ethyl]-acetamide (26b): (Procedure same as 26a)

2-(4-Phenyl-piperazin-1-yl)-ethylamine 4a (0.5 g, 2.43 mmol) was reacted with (3-Nitro-phenyl)-acetyl chloride (0.58 g, 2.92 mmol) in dichloro methane to give a crude product, which was purified by chromatography (EtOAc/Hexane=9/1) to produce 26b: 0.83 g (92% yield) as a yellow solid (mp,: 115–116° C.). $^1$H NMR (CDCl$_3$, 400 MHz): δ2.51–2.57 (6H, m, (CH$_2$)$_3$N), 3.06–3.14 (4H, m, (CH$_2$)$_2$NPh), 3.36–3.39 (2H, m, CH$_2$—NHCO), 3.65 (2H, s, CH$_2$Ar), 6.16 (1H, bs, NHCO), 6.85–6.91(2H, m, ArH), 7.25–7.29 (3H, m, ArH), 7.50 (1H, t, J=8.4, ArH), 7.65 (1H, d, J=7.6, ArH), 8.11–8.15 (2H, m, ArH).

[2-(4-nitro-phenyl)-ethyl]-[2-(4-phenyl-piperazin-1-yl)-ethyl]-amine (27a):

To a stirred solution of NaBH$_4$ (0.449 g, 11.81 mmol) in 50 mL of dry THF at 0° C. under N$_2$ was added dropwise 48% w/w BF$_3$ ether complex (1.47 mL, 11.68 mmol). The cooling bath was removed and the solution was stirred for 1 h at room temperature. Into the above was added dropwise a solution of 2-(4-nitro-phenyl)-N-[2-(4-phenyl-piperazin-1-yl)-ethyl]-acetamide 26a (0.55 g, 1.49 mmol) dissolved in THF (5 mL). The reaction mixture was refluxed for 6 h. After the solution cooled to room temperature, methanol (5 mL) was added slowly. The solvent was removed under reduced pressure and 10% HCl/MeOH (25 mL) was added to the residue and the solution refluxed for 1 h. Solid NaHCO$_3$ was added and methanol was removed in vacuo. The mixture was extracted with EtOAc. The combined organic phase was dried over Na$_2$SO$_4$ and evaporated to give the crude product which was purified by chromatography (EtOAc/MeOH=4/1) to give 27a: 0.385 g (73% yield) as a colorless oil. $^1$H NMR (CDCl$_3$, 400 MHz): δ1.62 (1H, bs, NH), 2.50 (2H, t, J=5.6 Hz, CH$_2$—CH$_2$NH), 2.58 (4H, t, J=4.8 Hz, (CH$_2$)$_2$N), 2.76 (2H, t, J=5.6 Hz, CH$_2$Ar), 2.90–2.96 (4H, m, (CH$_2$)$_2$NH), 3.14 (4H, t, J=4.8 Hz, (CH$_2$)$_2$NPh), 6.85 (1H, t, J=7.2, ArH), 6.90 (2H, d, J=9.2, ArH), 7.25 (2H, t, J=9.2, ArH), 7.37 (2H, d, J=8.8, ArH), 8.15 (2H, d, J=8, ArH).

[2-(4-nitro-phenyl)-ethyl]-[2-(4-phenyl-piperazin-1-yl)-ethyl]-amine (27b): (Procedure same as 27a)

2-(3-nitro-phenyl)-N-[2-(4-phenyl-piperazin-1-yl)-ethyl]-acetamide 26b (0.53 g, 1.43 mmol) was reacted with the stirred solution of NaBH$_4$ (0.433 g, 11.39 mmol) and 48% w/w BF$_3$ ether complex (1.42 ml, 11.28 mmol) in dry THF to produce a crude product, which was purified by chromatography (EtOAc)/MeOH=4/1) to give 27b: 0.375 g (74% yield) as a colorless oil. $^1$H NMR (CDCl$_3$, 400 MHz): δ 1.62 (1H, bs, NH), 2.52–2.59 (6H, m, (CH$_2$)$_2$N), 2.77 (2H, t, J=5.6, CH$_2$Ar), 2.90–2.98 (4H, m, (CH$_2$)$_2$NH), 3.13 (4H, t, J=5.6, (CH$_2$)$_2$NPh), 6.85 (1H, t, J=7.2, ArH), 6.90 (2H, d, J=8.4 Hz, ArH), 7.2 (2H, t, J=9.2, ArH), 7.45 (1H, t, J=8 Hz, ArH), 7.55 (1H, d, J=7.2, ArH), 8.05 (1H, d, J=8 Hz, ArH), 8.09 (1H, s, ArH).

N-[2-(4-Nitro-phenyl)-ethyl]-N-[2-(4-phenyl-piperazin-1-yl)-ethyl]-propionamide (28a):

To a stirred solution of [2-(4-nitro-phenyl)-ethyl]-[2-(4-phenyl-piperazin-1-yl)-ethyl]-amine 27a (0.375 g, 1.05 mmol), Et$_3$N (0.267 g, 2.64 mmol) in 25 mL of dry CH$_2$Cl$_2$ under nitrogen at 0° C. was added a solution of propionyl chloride (0.137 g, 1.48 mmol). The temperature was allowed to rise to room temperature, the mixture stirred for 2 h, and then washed with water. The aqueous layer was extracted with dichloromethane. The combined organic phase was dried (Na$_2$SO$_4$) and concentrated. The crude product was purified by column chromatography over silica gel (EtOAc/Hex=9/1) to give 28a as a colorless oil: 0.39 g (89% yield). $^1$H NMR (CDCl$_3$, 400 MHz): δ 1.16 (3H, t, J=7.2, CH$_3$), 2.38 (2H, q, J=7.2, CH$_2$), 2.51 (2H, t, J=7.2 Hz, CH$_2$Ar), 2.62 (4H, t, J=4.8, (CH$_2$)$_2$N), 2.99 (2H, t, J=7.2, CH$_2$—CH$_2$NCO), 3.15–3.20 (4H, m, (CH$_2$)$_2$NHPh, 3.32 (2H, t, J=7.2, CH$_2$—CH$_2$Ar), 3.58 (2H, t, J=7.2, CH$_2$NCO), 6.83–6.93 (3H, m, ArH), 7.23–7.28 (2H, m, ArH), 7.34 (1H, d, J=8.0, ArH), 7.38 (1H, d, J=8.8, ArH, 8.15 (1H, d, J=8.8, ArH), 8.18 (1H, d, J=8.4, ArH).

N-[2-(3-nitro-phenyl)-ethyl]-N-[2-(4-phenyl-piperazin-1-yl)-ethyl]-propionamide (28b): (Procedure same as 28a)

[2-(4-nitro-phenyl)-ethyl]-[2-(4-phenyl-piperazin-1-yl)-ethyl]-amine 27b (0.375 g, 1.05 mmol) was reacted with propionyl chloride (0.137 g, 1.48 mmol) in presence of Et$_3$N (0.267 g, 2.64 mmol) in dry CH$_2$Cl$_2$ to produce a crude product, which was purified by chromatography (EtOAc/Hex=9/1) to give 28b: 0.398 g (92% yield) as a colorless oil. $^1$H NMR (CDCl$_3$, 400 MHz): δ 1.16 (3H, t, J=7.2 Hz, CH$_3$), 2.38 (2H, q, J=7.2 Hz, CH$_2$), 2.52 (2H, t, J=7.2 Hz, CH$_2$Ar), 2.62 (4H, t, J=4.8 Hz, (CH$_2$)$_2$N), 2.99 (2H, t, J=7.2 Hz, CH$_2$—CH$_2$NCO), 3.16–3.21 (4H, m, (CH$_2$)$_2$NHPh, 3.34 (2H, t, J=7.2 Hz, CH$_2$—CH$_2$Ar), 3.59 (2H, t, J=7.2 Hz, CH$_2$NCO), 6.83–6.88 (1H, m, ArH), 6.91 (2H, d, J=8 Hz, ArH), 7.23–7.30 (2H, m, ArH), 7.44–7.60 (2H, m ArH), 8.07–8.13 (2H, m, ArH).

4-(2-{[2-(4-Phenyl-piperazin-1-yl)-ethyl]-propyl-amino}-ethyl)-phenylamine (29a):

N-[2-(4-nitro-phenyl)-ethyl]-N-[2-(4-phenyl-piperazin-1-yl)-ethyl]-propionamide 28a (0.33 g, 0.80 mmol) was dissolved in dry EtOH (20 mL) and 10 wt % Pd/C (0.05 g) was added. The mixture was stirred for overnight under H$_2$ at 1 atm. Pressure. The reaction mixture was filtered through celite and filtrate was concentrated under reduced pressure and kept under vacuum for 1 h to give the corresponding aniline. In to the solution of the crude product in 15 ml dry THF was added 1(M) BH$_3$/THF (7 mL, 7 mmol). The reaction mixture was refluxed for 6 h. After the solution was cooled to room temperature, methanol (5 mL) was added slowly. The solvent was removed under reduced pressure and 10% HCl/MeOH (25 mL) was added into the residue and the solution was refluxed for 1 h. Solid NaHCO$_3$ was added and the methanol was removed in vacuo. The mixture was extracted with EtOAc. The combined organic phase was dried over Na$_2$SO$_4$ and evaporated to give the crude product which was purified by chromatography (EtOAc/MeOH=9/1) to give 29a as a colorless oil: 0.23 g (78% yield). $^1$H NMR (CDCl$_3$, 300 MHz): δ 0.89 (3H, t, J=7.2 Hz, CH$_3$), 1.50 (2H, q, J=7.2 Hz, CH$_2$), 2.48–2.57 (4H, m, CH$_2$Ar, (CH$_2$)N), 2.63–2.75 (10H, m, (CH$_2$)$_3$N, (CH$_2$)$_2$N), 3.20 (4H, t, J=4.8 Hz, (CH$_2$)$_2$NPh), 3.56 (2H, bs, NH$_2$), 6.62 (2H, d, J=8.7 Hz, ArH), 6.85 (1H, t, J=9.6 Hz, ArH), 6.91–6.99 (4H, m, ArH), 7.25 (2H, t, J=9 Hz, ArH). Free base was converted into its hydrochloride salt, mp 262–264° C. Elemental analysis calculated for C$_{23}$H$_{38}$N$_4$Cl$_4$,1.05 H$_2$O:C, 51.99; H, 7.60; N, 10.54. Found C,52.37; H,7.89; N,10.12.

3-(2-{[2-(4-Phenyl-piperazin-1-yl)-ethyl]-propyl-amino}-ethyl)-phenylamine (29b): (Procedure same as 29a)

N-[2-(3-nitro-phenyl)-ethyl]-N-[2-(4-phenyl-piperazin-1-yl)-ethyl]-propionamide 28b (0.33 g, 0.80 mmol) was reacted with H$_2$ in presence of 10 wt % Pd/C (0.05 g) to produce corresponding aniline, which was then reacted with 1(M) BH$_3$/THF (7 ml, 7 mmol) to produce a crude product. The crude product was purified by chromatography (EtOAc/MeOH=9/1) to give 29b as a colorless oil 0.248 g (81% yield). $^1$H NMR (CDCl$_3$, 400 MHz): δ 0.89 (3H, t, J=7.2 Hz, CH$_3$), 1.50 (2H, q, J=7.2 Hz, CH$_2$), 2.48–2.56 (4H, m, CH$_2$Ar, (CH$_2$)N), 2.61–2.74 (10H, m, (CH$_2$)$_3$N, (CH$_2$)$_2$N), 3.20 (4H, t, J=4.8 Hz, (CH$_2$)$_2$NPh), 3.60 (2H, bs, NH$_2$), 6.51–6.54 (2H, m, ArH), 6.57–6.61 (1H, m, ArH), 6.85 (1H, t, J=7.2 Hz, ArH), 6.92 (2H, d, J=8.8 Hz, ArH), 7.04–7.08 (1H, m, ArH), 7.24–7.28 (2H, m, ArH). Free base was converted into its hydrochloride salt, mp 278–284° C. Elemental analysis calculated for C$_{23}$H$_{38}$N$_4$Cl$_4$,0.0475 H$_2$O:C, 53.03; H, 7.54; N, 10.75. Found C,53.39; H,7.96; N,10.26.

4-Chloro-N-[4-(2-{[2-(4-phenyl-piperazin-1-yl)-ethyl]-propyl-amino}-ethyl)-phenyl]-benzenesulfonamide (30a):

To a stirred solution of 6a (0.04 g, 0.01 mmol) and Et$_3$N (0.033 g, 0.32 mmol) in dry DMF (5 ml) under nitrogen gas was added 4-Chloro-benzenesulfonyl chloride and allowed to stir overnight. Water was added to the reaction mixture and extracted thrice with diethyl ether. The combined organic phase was washed with saturated sodium chloride, dried (Na$_2$SO$_4$) and concentrated. The crude product was purified by chromatography (EtOAc/MeOH=4/1) to produce 30a: 0.042 (75% yield) as a colorless oil. $^1$H NMR (CDCl$_3$, 300 MHz): δ 0.85 (3H, t, J=7.2 Hz, CH$_3$), 1.45 (2H, q, J=7.2 Hz, CH$_2$), 2.43–2.51 (4H, m, CH$_2$Ar, (CH$_2$)N), 2.61–2.69 (10H, m, (CH$_2$)$_3$N, (CH$_2$)N), 3.19 (4H, t, J=4.8 Hz, (CH$_2$)$_2$NPh), 6.85 (1H, t, J=7.2 Hz, ArH), 6.91–6.96 (3H, m, ArH), 7.08 (3H, d, J=8.4 Hz, ArH), 7.23–7.29 (2H, m, ArH), 7.38 (2H, d, J=8.4 Hz, ArH), 7.62–7.66 (2H, d, J=8.7 Hz, ArH). Free base was converted into its hydrochloride salt, mp 224–226° C. Elemental analysis calculated for C$_{29}$H$_{40}$Cl$_4$N$_4$O$_2$S, 0.25H$_2$O: C, 53.17; H, 6.23; N, 8.55. Found C,53.19; H,6.43; N,8.15.

4-Chloro-N-[3-(2-{[2-(4-phenyl-piperazin-1-yl)-ethyl]-propyl-amino}-ethyl)-phenyl]-benzenesulfonamide (30b): (Procedure same as 30a)

29b (0.05 g, 0.136 mmol), Et$_3$N (0.05 mL, 0.341 mmol) and 4-Chloro-benzenesulfonyl chloride (0.043 g, 0.2046 mmol) were reacted (procedure same as for 7a) to afford the title product 30b (0.058 g, 78%) as a colorless oil. $^1$H NMR (CDCl$_3$, 300 MHz): δ0.88 (3H, t, J= 7.3 Hz , CH$_3$), 1.45 (2H, q, J=7.1 Hz, CH$_2$), 1.7 (1H, bs, NH), 2.45–2.55 (4H, m, CH$_2$Ar, (CH$_2$)N), 2.62–2.71 (10H, (CH$_2$)$_3$N, (CH$_2$)$_2$N), 3.21 (4H, t, J=4.8 Hz, (CH$_2$)$_2$NPh), 6.86 (1H, t, J=7.2 ArH), 6.91–6.95 (3H, m, ArH), 7.00 (2H, d, J=7.8, ArH), 7.14–7.19 (3H, m, ArH), 7.39 (2H, d, J=8.7 Hz, ArH), 7.67 (2H, d, J=8.7 Hz, ArH). The free base was converted into its hydrochloride salt, mp 220–224° C. Elemental analysis calculated for C$_{29}$H$_{40}$Cl$_4$N$_4$O$_2$S,1.5H$_2$O; C=51.41; H=6.39; N=8.27. Found C=51.13; H=6.24; N=7.78.

APPENDIX

References:

1. Civelli, O., Bunzow, J. R., Grandy, D. K., Molecular Diversity of the Dopamine Receptors. ANNU. REV. PHARMACOL. TOXICOL, 32, 281–307, 1993.

2. Seeman, P., Tol Van, H., Dopamine Receptor Pharmacology. TIPS, 15, 264–270, 1994.

3. Kebabian, J. W., Calne, D. N., Multiple Receptors for Dopamine. NATURE, 277, 93–96, 1979.

4. Sokoloff, P., Giros, B., Martres, M.-P., Bouthernet, M.-L., Schwartz, J.-C, Molecular Cloning and Characterization of a Novel Dopamine Receptor (D3) as a Target for Neuroleptics. NATURE, 347, 146, 1990.

5. Giros, B., Matres. M.P., Sokoloff, P., Scwartz, J.C.R. ACAD. SCI, [III] 1990, 311, 501.

6. Sokoloff, P. et. al., Dopamine Receptors and Transporter Pharmacology, Structure and Function (Niznik, H. B., ed), pp 165- , Marcel Dekker.

7. Livingstone, C. D., Strange, P. G., Naylor, L. H., Molecular Modeling D2-like Dopamine Receptors. BIOCHEM. J. 287, 277–282, 1992.

8. Seeman, P., SYNAPSE, 1, 133–152, 1987.

9. Jenner, P., Marsden, C. D., Drugs in Central Nervous System Disorders, Horwell, D. C., Ed., Marcel Dekker: New York 1985, 149–262.

10. Landwehr, B., Mengod, G., Palcios, J.M., MOL. BRAIN.RES., 18, 187-, 1993.

11. Sokoloff, P., Martres, M-P., Giros, B., Bouthenet, M-L., Schwartz, J-C., BIOCHEM.PHARMACOL. 43,659-, 1992.

12. Schwartz, J-C., Levesque, D., Martes, M-P., Sokoloff, P., CLIN. NEUROPHARMACOL. 16, 295-, 1993.

13. Levant, B., The D3 Dopamine Receptor: Neurobiology and Potential Clinical Relevance, PHARMACOL. REV., 49, 231–252, 1997.

14. Caine, S. B., Koob, G. F., Modulation of Cocaine Self-administration in the Rat Through D-3 Dopamine Receptors, SCIENCE, 260, 1814–1816, 1993.

15. Caine, S. B., Koob, G. F., Pretreatment with the Dopamine Agonist 7-oh-dpat Shifts the Cocaine Self-Administration Dose Effect Function to the Left under Different Schedules in the Rat, BEHAV. PHARMACOL., 6, 333–347, 1995.

16. Pilla, M., Perachon, S., Sautel, F., Garrido, F., Mann, A., Wermuth, C., Schwartz, J-C., Everitt, B. J., Sokoloff, P., Selective Inhibition of Cocaine-seeking Beahviour by a Partial Dopamine D3 Receptor Agonist. NATURE, 400, 371–375, 1999.

17. Canon, J. G., Lee, T., Goldman, H. D., Costall, B., Naylor, R. J., Cerebral Dopamine Agonist Properties of Some 2-aminotetralin Derivatives after Peripheral and Intracerebral Administration, J. MED.CHEM., 20, 1111–1116, 1977.

18. McDermed, J., McKenzie, G., Phillips, A., Synthesis and Pharmacology of Some 2aminotetralins. Dopamine Receptor Agonists, J. MED. CHEM. 18, 362–367, 1975.

19. McDermed, J. D., McKenzie, G. M., Freeman, H. S., Synthesis and Dopaminergic Activity of (±)-, (+)- , and (−) -2-dipropylamino-5-hydroxy-1,2,3,4-tetrahydronapthalene, J. MED. CHEM. 19,547–549, 1976.

20. Hacksell, U., SVENSSON, U., Nilsson, J. L. G., Hjorth, S., Carlsson, A., Wikstrom, H., Lindberg, Sanchez, D., N-Alkylated 2-aminotetralins: Central Dopamaine-receptor Stimulating Activity, J. MED. 22,1469–1475, 1979.

21. Levesque, D., Diaz, J., Pilon, C., Martres, M.-P., Giros, B., Souil, E., Schott, D., Morgat, J.-L. Schwartz, J.-C., Sokoloff, P., Identification, Characterization, and Localization of the Dopamine $D_3$ Receptor in Rat Brain Using 7-[$_3$H]hydroxy-N,N-di-n-propyl-2-aminotetralin. PROC. NATL. ACAD. SCI. U.S.A., 89, 8155–8159, 1992.

22. Alexander van Vliet, L., Tepper, P. G., Dijkstra, D., Damsma, G., Wikstrom, H., Pugsly, T. A., Akunne, H. C., Heffner, T. G., Glase, S. A., Wise, L. D., Affinity for Dopamine $D_2$, $D_3$ and $D_4$ Receptors of 2-aminotetralins. Relevance of $D_2$ Agonist Binding for Determination of Receptor Subtype Selectivity, J. MED. CHEM. 39, 4233–4237, 1996.

23. John Murray, P., Harrison, L. A., Johnson, M. R., Robertson, G. M., Scopes, D. I., Bull, D. R., Graham, E. A., Hayes, A. G., Kilpatrick, G. J., Dass, I. D., Large, C., Sheehan, M. J., Stubbs, C. M., Turpin, M. P., A Novel Series of Arylpiperazines with High Affinity and Selectivity for the Dopamine $D_3$ Receptor, BIOORG. MED. CHEM. LETT., 5,219–222, 1995.

24. Teran, C., Santana, L., Uriarte, E., Fall, Y., Unelius, L., Tolf, B-R, Phenylpiperazine Derivatives with Strong Affinity for 5HT1a, D2A and D3 Receptors, BIOORG. MED. CHEM. LETT., 8, 3567–3570, 1998.

25. Boyfield, I., Coldwell, M. C., Hadley, M. S., Johnson, C. N., Riley, C. J., Scott, E. E., Stacey, R., Stemp, G., Thewlis, K. M., A Novel Series of 2-aminotetralins with High Affinity and Selectivity for the Dopamine $D_3$ Receptor. BIOORG. MED. CHEM. LETT., 7, 1995–1998, 1997.

26. Yuan, J., Chen, X., Brodbeck, R., Primus, R., Braun, J., Wasley, J. F., Thurkauf, A., NGB 2904 and NGB 2849: Two Highly Selective Dopamine, $D_3$ Receptor Antagonist. BIOORG. MED. CHEM. LETT., 8, 2715–2718, 1998.

27. Homan, E. J., Copinga, S., Elfstrom, L., Veen, T., Hallema, J-P., Mohell, N., Unelius, L., Johansson, R., Wilkstrom, H. V., Grol, C. J., 2-aminotetralin-derived Substituted Benzamide with Mixed Dopamine $D_2$, $D_3$, and Serotonin 5-HT1A Receptor Binding Properties: A Novel Class of Potential Atypical Antipsychotic Agents, BIOORG. MED. CHEM., 6, 2111–2126, 1998.

28. Avenell, K. Y., Boyfield, I., Hadley, M. S., Johnson, C. N., Nash, D. J., Riley G. J., Stemp, G., Heterocyclic Analogues of 2-aminotetralins with High Affinity and Selectivity for the Dopamine $D_3$ Receptor, BIOORG. MED. CHEM. LETT. 9, 2715–2720, 1999.

29. Pugsley, T. A., Davis, H. C. Akunne, H. C., Mackenzie, R. G., Shih, Y. H., Damsma, G., Wikstrom, H., Whetzel, S. Z., Georgic, L. M., Cooke, L. W., Dematos, S. B., Corbin, A. E. Glase, S. A., Wise, L. D., Dijkstra, D., Heffner, T. G., J. PHARMACOL. EXP. THER., 275, 1355–1366, 1995.

30. Pilon, C., Levesque, D., Dimitriadou, V., Griffon, N., Martres, M. P., Schwartz, J. C., and Sokoloff, P., DUR. J. PILARMACOL., 268:129–139, 1994.

31. Millan, M. J. et. al., J. PHARMACOL. EXP. THER., 286, 1341–1355, 1998.

32. Ravina, E. et al., J. MED. CHEM., 43, 4678–4693, 2000.

33. Watts, V. J., Lawler, C. P., Knoerzer, T., Mayleben, M. A., Neve, K. A., Nichols, D. E., Mailman, R. B., EUR. J. PHARMACOL., 239, 271–273, 1993.

34. Dutta, A. K., Fei, X.-S., Reith, M. E. A., BIORG. MED. CHEM. LETT., 12:4:619-6, 2002.

35. Kula, N. S. et al., CELL. MOL. NEUROBIOL., 14, 185–191, 1994.

What is claimed is:

1. A compound exhibiting CNS activity in mammalian species, having the structure

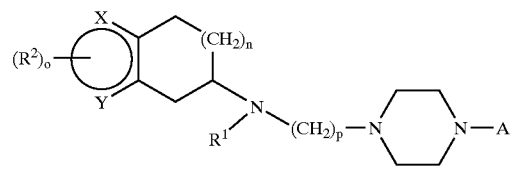

wherein A is an optionally heterocyclic 5 or 6 membered aromatic ring system;

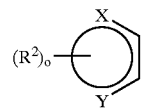

is an optionally heteroevelic 5 or 6 membered aromatic ring structure wherein X and Y are moieties which complete said 5 or 6 membered aromatic ring system.

$R^2$ is selected from the group consisting of $C_{1-8}$ alkyl, $C_{2-8}$ alkenyl, $C_{2-8}$ alkynyl, $C_{4-8}$ cycloalkyl, $C_{4-8}$ cycloalkenyl; $C_{6-10}$ aryl, —$NR^4_q$ where $R^4$ individually are H, $C_{1-8}$ alkyl, $C_{2-8}$ alkenyl, $C_{4-8}$ cycloalkyl, $C_{4-8}$ cycloalkenyl, $C_{6-20}$ aryl and q is 3 or 4, with the proviso that when q is 4, the group bears a positive formal charge; —$NR^4$—C(O)—$R^4$, —$NR^4$—C(O)—$NR^4_2$ wherein the above hydrocarbon groups may optional be substituted with —CN, $C_{1-4}$ lower alkyl, —$OR^4$, and halo, or two $R^2$ together may form a fused ring system, o is an integer from 0 to 4, the upper limit of o bounded by the number of available substitutent sites on said optionally heterocyclic 5 or 6 membere aromatic ring structure;

n is an integer from 0 to 2;

$R^1$ is selected from the group consisting of $C_{18}$ alkyl, $C_{2-8}$ alkenyl, $C_{2-8}$ alkynyl, $C_{4-8}$ cycloalkyl, $C_{4-8}$ cycloalkenyl, $C_{6-10}$ aryl, each of the foregoing alkyl, a kenyl, alkynyl, cycloalkyl, cycloalkenyl, and aryl groups optionally halo substituted and/or substituted by —CN, $C_{1-4}$ lower alkoxy, $C_{1-4}$ acyloxy, $C_{1-4}$ acyl, or —C(O)—$R^4$;— —NH—$SO_2$—$NR^4$ where $R^5$ is $C_{1-8}$ alkylene and r is 2 or 3, with the proviso that when r is 3, the nitrogen of the $NR^4_r$ group will bear a positive formal charge; —$R^5$—NH—C(O)—$R^4$; —$R^5$—$NR^4_r$, —$R^5$—Ar where Ar is an aryl ring system, optionally including one or more heteroatoms; and p is 1 to 4;

wherein one $(CH_2)_n$ group may be replaced by O or S;

or a pharmaceutically acceptable salt thereof.

2. A compound exhibiting CNS activity in mammalian species, having the structure:

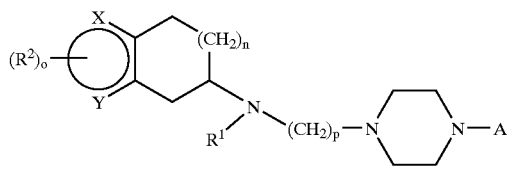

is an optionally heterocyclic 5 or 6 membered aromatic ring structure wher in X and Y are moieties which complete said 5 or 6 membered aromatic ring system:

$R^2$ is selected from the group consisting of $C_{1-8}$ alkyl, $C_{2-8}$ alkenyl, $C_{2-8}$ alkynyl, $C_{4-8}$ cycloalkyl, $C_{48}$ cycloalkenyl; $C_{6-10}$ aryl, —$NR^4_q$ where $R^4$ individually are , $C_{1-8}$ alkyl, $C_{2-8}$ alkenyl, $C_{4-8}$ cycloalkyl, $C_{4-8}$ cycloalkenyl, $C_{6-10}$ aryl and q is 3 or 4, with the proviso that when q is 4, the group bears a positive formal charge; —$NR^4$—C(O)—$R^4$, —$NR^4$—C(O)—$NR^4_2$ wherein the above hydrocarbon groups may optionally be substituted with —CN, $C_{1-4}$ lower ikyl, —$OR^4$, and halo;

$R^1$ is selected from the group consisting of $C_{1-8}$ alkyl, $C_{2-8}$ alkenyl, $C_{2-8}$ alkynyl, $C_{4-8}$ cycloalkyl, $C_{4-8}$ cycloalkenyl, $C_{6-10}$ aryl, each of the foregoing alkyl, alkenyl, alkynyl, cycloalkyl, cycloalkeny, and aryl groups optionally halo substituted and/or substituted by —CN, $C_{1-4}$ lower alkoxy, acyloxy, acyl, or —C(O)—$R^4$; —$R^5$—NH—$SO_2$—$NR^4$ here $R^5$ is $C_{1-8}$ alkylene and r is 2 or 3, with the proviso that when r is 3, the nitrogen of the $R^4_r$ group will bear a positive formal charge; —$R^5$—NH—C(O)—$R^4$; —$R^5$—$NR^4_r$, —$R^5$—Ar where Ar is an aryl ring system, optionally including one or more heceroatoms; and A is an optionally heterocyclic aromatic ring system containing to 4 optionally fused aromatic five or six membered rings, one or more rings optionally substituted by one or more $C_{1-4}$ alkyl, $C_{2-4}$A alkenyl, $C_{5-7}$ cycloalkyl, $C_{5-7}$ cycloalkenyl, halo, $C_{1-4}$ aldehydro, or —$NR^4_q$ groups, or a pharmaceutically acceptable salt thereof.

3. The compound of claim 1 having the structure

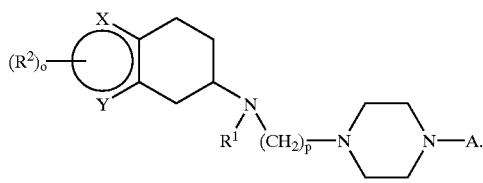

4. The compound of claim 2 having the structure

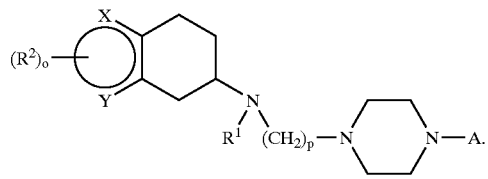

5. A compound exhibiting CNS activity in mammalian species, having a structure selected from the group consisting of

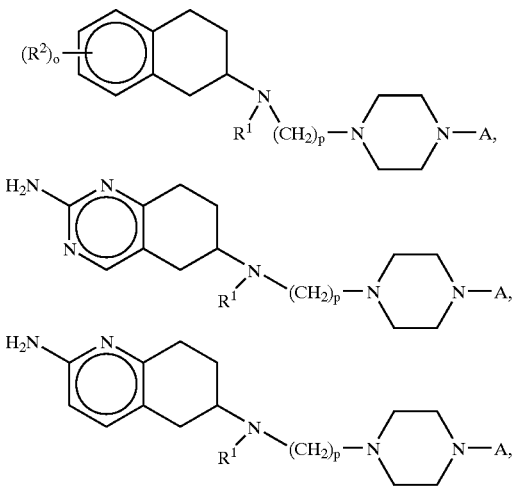

and wherein A is an optionally heterocyclic 5 or 6 membered aromatic ring system

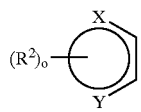

is an optionally heterocyclic 5 or 6 membered aromatic ring structure wherein X and Y are moieties which complete said 5 or 6 membered aromatic ring system:

$R^2$ is selected from the group consisting of $C_{1-8}$ alkyl, $C_{2-8}$ alkenyl, $C_{2-8}$ alkynyl, $C_{4-8}$ cycloalkyl, $C_{4-8}$ cycloalkenyl; $C_{6-10}$ aryl, —$NR^4_q$ where $R^4$ individually ar H, $C_{1-8}$ alkyl, $C_{2-8}$ alkenyl, $C_{4-8}$ cycloalkyl, $C_{4-8}$ cycloalkenyl, $C_{6-10}$ aryl and q is 3 or 4, with the proviso that when q is 4, the group bears a positive formal charge; —$R^4$—C(O)—$R^4$, —$NR^4$—C(O)—$NR^4_2$ wherein the above hydrocarbon groups may optionally be substituted with —CN, $C_{1-4}$ lower alkyl, —$OR^4$, and halo; or two $R^2$ together may form a fused ring system, o is an integer from 0 to 4, the upper limit of o bounded by the number of available substitutent sites on said optionally heterocyclic 5 or 6 membered aromatic ring structure;

n is an integer from 0 to 2;

$R^1$ is selected from the group consisting of $C_{1-8}$ alkyl, $C_{2-8}$ alkenyl, $C_{2-8}$ alkynyl, $C_{4-8}$ cycloallcyl, $C_{4-8}$ cycloalkenyl, $C_{6-10}$ aryl, each of the foregoing alkyl, alkenyl, alkynyl, cycloalkyl, cycloalkenyl, and aryl groups optionally halo substituted and/or substituted by —CN, $C_{1-4}$ lower alkoxy, $C_{1-4}$ acyloxy, $C_{1-4}$ acyl, or —C(O)—$R^4$; —R —NH—$SO_2$—$NR^4_r$ where $R^5$ is $C_{1-8}$ alkylene and r is 2 or 3, with the proviso that when r is 3, the nitrogen of the $NR^4_r$ group will bear a positive formal charge; —$R^5$—NH—C(O)—$R^4$; —$R^5$—$NR^4_r$, —$R^5$—Ar where Ar is an aryl ring system, optionally including one or more hetrroatoms; and;

p is 1 to 4;

wherein one $(CH_2)_n$ group may be replaced by O or S;

or a pharmaceutically acceptable salt thereof.

6. The compound of claim 2 wherein A is selected form the group consisting of phenyl, 2-methoxyphenyl, 2,3-dichiorophenyl, 4-(methylsulfonamino)phenyl, and biphenyl.

7. A compound of claim 2 having the structure

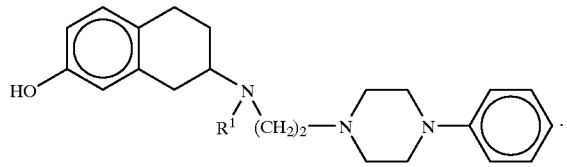

8. A compound of claim 2 having the structure

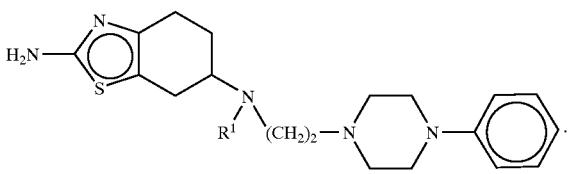

* * * * *

UNITED STATES PATENT AND TRADEMARK OFFICE
CERTIFICATE OF CORRECTION

PATENT NO. : 6,982,332 B2
DATED : January 3, 2006
INVENTOR(S) : Aloke K. Dutta

It is certified that error appears in the above-identified patent and that said Letters Patent is hereby corrected as shown below:

Column 24,
Line 54, delete "$C_6$-$C_{20}$ aryl" and insert -- $C_6$-$C_{10}$ aryl --.
Line 62, delete "membere" and insert -- membered --.
Line 65, delete "$C_{18}$ alkyl" and insert -- $C_{1-8}$ alkyl --.
Line 67, delete "a kenyl" and insert -- alkenyl --.

Column 25,
Line 4, delete "NH-$SO_2$-$NR^4$-" and insert -- -$R^5$-NH-$SO_2$-$NR^4$- --.
Line 29, delete "$C_{48}$ cycloalkenyl" and insert -- $C_{4-8}$ cycloalkenyl --.
Line 36, delete "lower ikyl" and insert -- lower alkyl --.
Line 43, delete "acyloxy, acyl" and insert -- $C_{1-4}$ acyloxy, $C_{1-4}$ acyl --.
Line 46, delete "$R^4$" and insert -- $NR^4$ --.
Line 51, delete "containing to 4" and insert -- containing 1 to 4 --.
Line 53, delete "$C_{2-4}$ A alkenyl" and insert -- $C_{2-4}$ alkenyl --.

Column 26,
Line 51, delete "ar H" and insert -- are H --.
Line 55, delete "-$R^4$-C(O)-$R^4$" and insert -- -$NR^4$-C(O)-$R^4$ --.
Line 66, delete "$C_{4-8}$ cycloalleyl" and insert -- $C_{4-8}$ cycloalkyl --.

Column 27,
Line 5, delete "-R-NH-$SO_2$-$NR^4_r$" and insert -- $R^5$-NH-$SO_2$-$NR^4_r$ --.
Line 20, delete "dichiorophenyl" and insert -- dichorophenyl --.

Signed and Sealed this

Eleventh Day of April, 2006

JON W. DUDAS
*Director of the United States Patent and Trademark Office*